(12) United States Patent
Yoshii

(10) Patent No.: US 8,843,318 B2
(45) Date of Patent: Sep. 23, 2014

(54) WATER QUALITY MEASURING METHOD, WATER QUALITY MEASURING DEVICE, AND WATER QUALITY MEASURING PROGRAM FOR MARINE SURFACE LAYERS

(75) Inventor: Takumi Yoshii, Chiba (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 415 days.

(21) Appl. No.: 13/376,536

(22) PCT Filed: Jun. 16, 2010

(86) PCT No.: PCT/JP2010/004010
§ 371 (c)(1),
(2), (4) Date: Dec. 6, 2011

(87) PCT Pub. No.: WO2010/150490
PCT Pub. Date: Dec. 29, 2010

(65) Prior Publication Data
US 2012/0078516 A1    Mar. 29, 2012

(30) Foreign Application Priority Data

Jun. 22, 2009  (JP) ................................. 2009-147643
Feb. 26, 2010  (JP) ................................. 2010-042059

(51) Int. Cl.
*G06F 19/00*     (2011.01)
*G01K 11/00*    (2006.01)
*G01N 33/18*    (2006.01)
*G01S 13/95*     (2006.01)

(52) U.S. Cl.
CPC .............. *G01K 11/006* (2013.01); *G01N 33/18* (2013.01); *G01S 13/951* (2013.01)
USPC ........... 702/2; 114/72; 114/61.29; 114/61.27; 114/77 R; 701/21; 701/532; 440/58

(58) Field of Classification Search
CPC ...... B63C 11/42; B63B 27/36; G01K 11/006; G01S 13/951; G01N 33/18
USPC ......... 702/2; 440/58; 114/72, 312, 337, 77 R, 114/61.3, 61.31, 61.29, 61.27, 61, 31, 114/144 A; 701/21, 532
See application file for complete search history.

(56) References Cited

U.S. PATENT DOCUMENTS 6,269,763 B1 *  8/2001  Woodland ..................... 114/382
6,427,615 B1 *  8/2002  Ku ............................... 114/77 R (Continued)

FOREIGN PATENT DOCUMENTS

JP    2004-85394 A    8/2002
JP    2005-321269 A   5/2004
JP    2007248293      9/2007

OTHER PUBLICATIONS

Takumi Yoshii et al., Central Research Institute of Electric Power Industry; Kenyu Hokokusho, Jun. 2008, V07017.

(Continued)

*Primary Examiner* — Carol S Tsai
(74) *Attorney, Agent, or Firm* — Notaro, Michalos & Zaccaria P.C.

(57) ABSTRACT

To measure salinity and water temperature in a marine surface layer using data obtained by a marine radar, a deviation $\Delta S'$ between effect of an ocean wave on received power $RSI_0'$ in a reference time zone and effect of the ocean wave on received power $RSI_m'$ in a measurement time zone is estimated, a deviation $\Delta s'$ between effect of the ocean wave on the received power $RSI_0'$ in the reference time zone and effect of the ocean wave on the received power in an electrical conductivity variable time zone is estimated, a regression function $f(\sigma)$ of a relationship between received power obtained by subtracting the deviation $\Delta s'$ from the received power in the electrical conductivity variable time zone and electrical conductivity $\sigma$ in the electrical conductivity variable time zone is estimated, and a value of electrical conductivity $\sigma_c$ in a measurement time zone is estimated, thereby calculating practical salinity.

12 Claims, 15 Drawing Sheets

(56) References Cited

U.S. PATENT DOCUMENTS 7,434,523 B2 * 10/2008 Kingsbury ............... 114/61.29
2002/0092458 A1 * 7/2002 Ku ............................ 114/312

OTHER PUBLICATIONS

Takumi Yoshii et al., Central Research Institute of Electric Power Industry; Kenyu Hokokusho, Sep. 2009, V09003.

Takumi Yoshii et al., Central Research Institute of Electric Power Industry; Kenyu Hokokusho, May 2010, V09038.

Takumi Yoshii et al., Discussion about Factor Affecting Data Acquisition Ration in DBF Marine Radar Using VHF band, Hydraulic Engineering Collected Papers, vol. No. 52, 2008.

* cited by examiner

ELECTRIC WAVE WAVELENGTH 12.2 m (25 MHz)

ELECTRIC WAVE WAVELENGTH 7.2 m (41.9 MHz)

WATER QUALITY MEASURING METHOD, WATER QUALITY MEASURING DEVICE, AND WATER QUALITY MEASURING PROGRAM FOR MARINE SURFACE LAYERS

TECHNICAL FIELD

The present invention relates to a water quality measuring method, a water quality measuring device, and a water quality measuring program for marine surface layers. More particularly, the present invention relates to a technology for measuring salinity and a water temperature of a marine surface layer by using an observation result of a marine radar.

BACKGROUND ART

As measurement of water quality or flowage in a marine area in the range of several km to several tens of km, on-site direct measurement, e.g., shipboard measurement or measurement at anchorage points predominates. However, such direct measurement requires a tremendous cost in terms of manpower or expenses in order to simultaneously measure various kinds of data covering a widespread marine area. Therefore, it is difficult to obtain surface data from a target of a marine area in the range of several km to several tens of km.

As a method of obtaining surface data based on simultaneous measurement from a target of marine area in the range of several km to several tens of km, there is a method using a marine radar. Further, as a conventional method of measuring a flow velocity distribution as marine surface data by using a marine radar, there is a method of processing reflected waves obtained by emitting electric waves to a sea surface as a video signal, generating a high-resolution radar image from this video signal, and calculating a flow velocity distribution based on this high-resolution radar image (Patent Literature 1).

CITATION LIST

Patent Literature

Patent Literature 1: Japanese Unexamined Patent Application Publication No. 2007-248293

SUMMARY OF INVENTION

Technical Problem

Since marine salinity or a water temperature changes density in seawater, it greatly affects a flow regime in a marine area and plays an extremely important role as a factor that characterizes a habitat environment of living things. Therefore, grasping the salinity or a water temperature in the marine widespread range can not only contribute to improvement in a prediction accuracy of a flow regime but also provide information that is very important and useful for, e.g., prediction of generation of red tides or prediction of generation/movement of living things.

However, in the method according to Patent Literature 1, a marine flow velocity distribution is measured using data obtained by the marine radar and, on the other hand, marine salinity or a water temperature is not measured. That is, there is no conventional technology that can obtain surface data from the marine area in the range of several tens of km based on simultaneous measurement using the marine radar while measuring the marine salinity or a water temperature using the data obtained by the marine radar.

It is, therefore, an object of the present invention to provide a water quality measuring method, a water quality measuring device, and a water quality measuring program for marine surface layers that use data obtained by a marine radar to enable measuring salinity and a water temperature in a marine surface layer.

Solution to Problem

To achieve this object, there is provided a salinity measuring method for marine surface layers according to the present invention comprising: a step of estimating a deviation $\Delta S'$ between effect of an ocean wave on primary scattering intensity $RSI_0'$ of received power observed by a marine radar in a reference time zone and effect of the ocean wave on primary scattering intensity $RSI_m'$ of received power in a measurement time zone by using data of the ocean wave or a wind velocity in the reference time zone in which electrical conductivity of seawater does not change and data of the ocean wave or the wind velocity in the measurement time zone in which water quality of the seawater is measured; a step of estimating a deviation $\Delta s'$ between the effect of the ocean wave on the primary scattering intensity $RSI_0'$ of the received power in the reference time zone and effect of the ocean wave on primary scattering intensity of the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function $f(\sigma)$ of a relationship between primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; a step of estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); a step of calculating electrical conductivity $\sigma(15)$ when a water temperature is 15° C. by using the value of the electrical conductivity $\sigma_c$ in the measurement time zone; a step of calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and a step of calculating practical salinity by using the value of the ratio $K_{15}$ of the electrical conductivity.

Further, a salinity measuring device for marine surface layers according to the present invention comprises: means for estimating a deviation $\Delta S'$ between effect of an ocean wave on primary scattering intensity $RSI_0'$ of received power observed by a marine radar in a reference time zone and effect of the ocean wave on primary scattering intensity $RSI_m'$ of received power in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the primary scattering intensity $RSI_0'$ of the received power in the reference time zone and effect of the ocean wave on primary scattering intensity of the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function f(σ) of a relationship between primary scattering intensity of the received power obtained by subtracting the deviation Δs' from the primary scattering intensity of the received power observed by the marine radar in the electrical conductivity variable time zone and electrical conductivity σ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); means for calculating electrical conductivity σ(15) when a water temperature is 15° C. by using the value of the electrical conductivity $\sigma_c$ in the measurement time zone; means for calculating a ratio $K_{15}$ of the electrical conductivity σ(15) of the seawater to electrical conductivity of a standard solution of a potassium chloride in a standard state of 15° C. and 1 atmosphere by using the electrical conductivity σ(15) when the water temperature is 15° C.; and means for calculating practical salinity by using the value of the ratio $K_{15}$ of the electrical conductivity.

Furthermore, in estimation of salinity in a marine area as a water quality measurement target using a value of received power observed by a marine radar in the marine area, a salinity measuring program for marine surface layers according to the present invention allows a computer to function as: means for estimating a deviation ΔS' between effect of an ocean wave on primary scattering intensity $RSI_0'$ of received power observed by the marine radar in a reference time zone and effect of the ocean wave on primary scattering intensity $RSI_m'$ of received power in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation Δs' between the effect of the ocean wave on the primary scattering intensity $RSI_0'$ of the received power in the reference time zone and effect of the ocean wave on primary scattering intensity of the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function f(σ) of a relationship between primary scattering intensity of the received power obtained by subtracting the deviation Δs' from the primary scattering intensity of the received power observed by the marine radar in the electrical conductivity variable time zone and electrical conductivity σ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); means for calculating electrical conductivity σ(15) when a water temperature is 15° C. by using the value of the electrical conductivity $\sigma_c$ in the measurement time zone; means for calculating a ratio $K_{15}$ of the electrical conductivity σ(15) of the seawater to electrical conductivity of a standard solution of a potassium chloride in a standard state of 15° C. and 1 atmosphere by using the electrical conductivity σ(15) when the water temperature is 15° C.; and means for calculating practical salinity by using the value of the ratio $K_{15}$ of the electrical conductivity.

Moreover, a water temperature measuring method for marine surface layers according to the present invention comprises: a step of estimating a deviation ΔS' between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; a step of estimating a deviation Δs' between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function f(σ) of a relationship between the received power obtained by subtracting the deviation Δs' from the received power observed by the marine radar in the electrical conductivity variable time zone and electrical conductivity σ in the electrical conductivity variable time zone; a step of estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and a step of estimating a value of a water temperature $T_c$ in the measurement time zone by using $\sigma_c=\sigma_0\{1+\alpha(T_c-T_0)\}$ (where $T_0$: a water temperature in the reference time zone, α: a temperature correction coefficient).

Additionally, a water temperature measuring device for marine surface layers comprises: means for estimating a deviation ΔS' between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation Δs' between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function f(σ) of a relationship between the received power obtained by subtracting the deviation Δs' from the received power observed by the marine radar in the electrical conductivity variable time zone and electrical conductivity σ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and means for estimating a value of a water temperature $T_c$ in the measurement time zone by using $\sigma_c=\sigma_0\{1+\alpha(T_c-T_0)\}$ (where $T_0$: a water temperature in the reference time zone, α: a temperature correction coefficient).

Further, in estimation of a water temperature in a marine area as a water quality measurement target using a value of received power observed by a marine radar in the marine area, a water temperature measuring program for marine surface layers according to the present invention allows a computer to function as: means for estimating a deviation ΔS' between effect of an ocean wave on received power $RSI_0'$ observed by the marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation Δs' between the effect of the ocean wave on the received power $RSI_0$' in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function f(σ) of a relationship between the received power obtained by subtracting the deviation Δs' from the received power observed by the marine radar in the electrical conductivity variable time zone and electrical conductivity σ in the electrical conductivity variable time zone; means for estimating a value of electrical conductivity $σ_c$ in the measurement time zone by using $RSI_0'-RSI_m'=ΔS'+\{f(σ_0)-f(σ_c)\}$ (where $σ_0$: electrical conductivity in the reference time zone); and means for estimating a value of a water temperature $T_c$ in the measurement time zone by using $σ_c=σ_0\{1+α(T_c-T_0)\}$ (where $T_0$: a water temperature in the reference time zone, α: a temperature correction coefficient).

Furthermore, a water temperature measuring method for marine surface layers according to the present invention comprises: a step of estimating a deviation ΔS' between effect of an ocean wave on received power $RSI_0$' observed by a marine radar in a reference time zone and effect of the ocean wave on received power $RSI_m$' in a measurement time zone by using data of the ocean wave or a wind velocity in the reference time zone in which electrical conductivity of seawater does not change and data of the ocean wave or the wind velocity in the measurement time zone in which water quality of the seawater is measured; a step of estimating a deviation Δs' between the effect of the ocean wave on the received power $RSI_0$' in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function f(σ) of a relationship between the received power obtained by subtracting the deviation Δs' from the received power observed by the marine radar in the electrical conductivity variable time zone and electrical conductivity σ in the electrical conductivity variable time zone; a step of estimating a value of electrical conductivity $σ_c$ in the measurement time zone by using $RSI_0'-RSI_m'=ΔS'+\{f(σ_0)-f(σ_c)\}$ (where electrical conductivity in the reference time zone); and a step of estimating a value of a water temperature $T_c$ in the measurement time zone by using $K_{15}=σ_c/[σ_{KCl}(15)\{1+α(T_c-15)\}]$ and $PS=0.008-0.1692K_{15}^{0.5}+25.3851K_{15}+14.0941K_{15}^{1.5}-7.0261K_{15}^2+2.708\ 1K_{15}^{2.5}$ (where $σ_{KCl}(15)$: electrical conductivity of a standard solution of a potassium chloride in a standard state of 15° C. and 1 atmosphere, α: a temperature correction coefficient, PS: salinity in the measurement time zone).

Moreover, a water temperature measuring device for marine surface layers according to the present invention comprises: means for estimating a deviation ΔS' between effect of an ocean wave on received power $RSI_0$' observed by a marine radar in a reference time zone and effect of the ocean wave on received power $RSI_m$' in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation Δs' between the effect of the ocean wave on the received power $RSI_0$' in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function f(σ) of a relationship between the received power obtained by subtracting the deviation Δs' from the received power observed by the marine radar in the electrical conductivity variable time zone and electrical conductivity σ in the electrical conductivity variable time zone; means for estimating a value of electrical conductivity $σ_c$ in the measurement time zone by using $RSI_0'-RSI_m'=ΔS'+\{f(σ_0)-f(σ_c)\}$ (where $σ_0$: electrical conductivity in the reference time zone); and means for estimating a value of a water temperature $T_c$ in the measurement time zone by using $K_{15}=σ_c/[σ_{KCl}(15)\{1+α(T_c-15)\}]$ and $PS=0.008-0.1692K_{15}^{0.5}+25.3851K_{15}+14.0941K_{15}^{1.5}-7.0261K_{15}^2+2.708\ 1K_{15}^{2.5}$ (where $σ_{KCl}(15)$: electrical conductivity of a standard solution of a potassium chloride in a standard state of 15° C. and 1 atmosphere, α: a temperature correction coefficient, PS: salinity in the measurement time zone).

Additionally, in estimation of a water temperature in a marine area as a water quality measurement target using a value of received power observed by a marine radar in the marine area, a water temperature measuring program for marine surface layers according to the present invention allows a computer to function as: means for estimating a deviation ΔS' between effect of an ocean wave on received power $RSI_0$' observed by the marine radar in a reference time zone and effect of the ocean wave on received power $RSI_m$' in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation Δs' between the effect of the ocean wave on the received power $RSI_0$' in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function f(σ) of a relationship between the received power obtained by subtracting the deviation Δs' from the received power observed by the marine radar in the electrical conductivity variable time zone and electrical conductivity σ in the electrical conductivity variable time zone; means for estimating a value of electrical conductivity $σ_c$ in the measurement time zone by using $RSI_0'-RSI_m'=ΔS'+\{f(σ_0)-f(σ_c)\}$ (where $σ_0$: electrical conductivity in the reference time zone); and means for estimating a value of a water temperature $T_c$ in the measurement time zone by using $K_{15}=σ_c/[σ_{KCl}(15)\{1+α(T_c-15)\}]$ and $PS=0.008-0.1692K_{15}^{0.5}+25.3851K_{15}+14.0941K_{15}^{1.5}-7.0261K_{15}^2+2.708\ 1K_{15}^{2.5}$ (where $σ_{KCl}(15)$: electrical conductivity of a standard solution of a potassium chloride in a standard state of 15° C. and 1 atmosphere, α: a temperature correction coefficient, PS: salinity in the measurement time zone).

Further, a salinity measuring method for marine surface layers according to the present invention comprises: a step of estimating a deviation Δs' between effect of an ocean wave on primary scattering intensity $RSI_0'$ of received power observed by a marine radar in a reference time zone and effect of the ocean wave on the primary scattering intensity of the received power in an electrical conductivity variable time zone by using data of the ocean wave or a wind velocity in the reference time zone that electrical conductivity of seawater does not change and data of the ocean wave or the wind velocity in the electrical conductivity variable time zone in which the electrical conductivity of the seawater varies; a step of estimating a regression function $f(\sigma)$ of a relationship between the primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; a step of estimating a value of electrical conductivity $\sigma_c$ in a measurement time zone by using a noise floor $RSIn_m'$ of the received power in the measurement time zone in which water quality of the seawater is measured and $RSI_0' - RSI_m' = \Delta S' + \{f(\sigma_0) - f(\sigma_c)\}$ (where $\sigma_0$: electrical conductivity in the reference time zone); a step of calculating electrical conductivity $\sigma(15)$ when a water temperature is 15° C. by using the value of the electrical conductivity $\sigma_c$ in the measurement time zone; a step of calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and a step of calculating practical salinity by using the value of the ratio $K_{15}$ of the electrical conductivity.

Furthermore, a salinity measuring device for marine surface layers according to the present invention comprises: means for estimating a deviation $\Delta s'$ between effect of an ocean wave on primary scattering intensity $RSI_0'$ of received power observed by a marine radar in a reference time zone and effect of the ocean wave on the primary scattering intensity of the received power in an electrical conductivity variable time zone by using data of the ocean wave or a wind velocity in the reference time zone that electrical conductivity of seawater does not change and data of the ocean wave or the wind velocity in the electrical conductivity variable time zone in which the electrical conductivity of the seawater varies; means for estimating a regression function $f(\sigma)$ of a relationship between the primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; means for estimating a value of electrical conductivity $\sigma_c$ in a measurement time zone by using a noise floor $RSIn_m'$ of the received power in the measurement time zone in which water quality of the seawater is measured and $RSI_0' - RSI_m' = \Delta S' + \{f(\sigma_0) - f(\sigma_c)\}$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and means for calculating practical salinity by using the value of the ratio $K_{15}$ of the electrical conductivity.

Moreover, in estimation of a water temperature in a marine area as a water quality measurement target using a value of received power observed by a marine radar in the marine area, a salinity measuring program for marine surface layers according to the present invention allows a computer to function as: means for estimating a deviation $\Delta s'$ between effect of an ocean wave on primary scattering intensity $RSI_0'$ of received power observed by the marine radar in a reference time zone and effect of the ocean wave on the primary scattering intensity of the received power in an electrical conductivity variable time zone by using data of the ocean wave or a wind velocity in the reference time zone that electrical conductivity of seawater does not change and data of the ocean wave or the wind velocity in the electrical conductivity variable time zone in which the electrical conductivity of the seawater varies; means for estimating a regression function $f(\sigma)$ of a relationship between the primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; means for estimating a value of electrical conductivity $\sigma_c$ in a measurement time zone by using a noise floor $RSIn_m'$ of the received power in the measurement time zone in which water quality of the seawater is measured and $RSI_0' - RSI_m' = \Delta S' + \{f(\sigma_0) - f(\sigma_c)\}$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and means for calculating practical salinity by using the value of the ratio $K_{15}$ of the electrical conductivity.

According to the water quality measuring method, the water quality measuring device, and the water quality measuring program for marine surface layers, based on the following theory and the knowledge obtained from examinations conducted by the present inventors, salinity and a water temperature in a marine surface layer can be obtained by using a value of received power observed by the marine radar.

(1) Outline of Observation using Marine Radar

The Marine radar is a device that emits electric waves to a sea surface and also receives electric waves scattered by the sea surface. The electric waves emitted to the sea surface are scattered by the sea surface. Scattering is a phenomenon that electromagnetic waves are newly generated due to polarization and current oscillation when the electromagnetic waves are applied to a scatter bank (Kenichi Okamoto: Global Environment Measurement, 1999).

When scattering occurs due to sea surface waves having a wavelength that is a half of a wavelength of transmitted electric waves, intensity of the scattered electric waves is characterized by being increased due to interference of the electric waves. This phenomenon is called Bragg scattering (Crombie, D. D.: Doppler Spectrum of Sea Echo at −13.56 Mc/s, Nature, Vol. 175, pp. 681-682, 1955). Further, electric waves produced by this Bragg scattering can be received, and information of a surface layer flow velocity and others of a marine area can be extracted from the received electric waves.

In the marine radar, electric waves having a wavelength corresponding to a double of wind waves that are apt to be produced on a sea surface are used so that the Bragg scattering can always occur on the sea surface. It is to be noted that electric waves in an HF band (specifically, 3 to 30 MHz) and electric waves in a VHF band (specifically, 30 to 300 MHz) are mainly used at home and abroad.

The electric waves transmitted from a transmitting station are scattered at various spots in a marine area in a transmitting direction and received by a observing station (it is to be noted that the transmitting station and the observing station are generally provided at the same spot). Since the received electric waves can be decomposed in distance directions by utilizing a fact that a time required for the received electric waves to reciprocate each distance differs, a spatial distribution of the electric waves in the transmitting direction can be grasped.

FIG. 3 shows an example of a received electric wave observed by the marine radar. An abscissa of FIG. 3 represents a Doppler frequency obtained by subtracting a frequency of a transmitted electric wave from that of the received electric wave, and a result obtained by plotting the received power with respect to the Doppler frequency is called a Doppler spectrum. It can be understood from FIG. 3 that peaks of the received electric wave in the Doppler spectrum appear around and on both sides of 0 Hz. It is considered that the peaks of the received power around 0 Hz are obtained as a result of reflection from a stationary object such as land.

The peaks on both the sides of 0 Hz are electric waves obtained by the Bragg scattering on a sea surface, and this scattering is called primary scattering (a black circle symbol and an outline circle symbol in FIG. 3). Two pieces of primary scattering appear because the Bragg scattering occurs in both a wave vanishing from the observing station and a wave approaching the same. It is to be noted that a surface layer flow velocity is calculated as a difference between a wave velocity calculated from the Doppler frequency leading to occurrence of the primary scattering and a wave velocity obtained from the theory of a deep-water wave.

In the present invention, primary scattering intensity (the black circle symbol in FIG. 3) in the received electric wave is basically used as received power, and an average value of noise values in the received electric wave is used when the primary scattering intensity cannot be clearly determined in a measurement time zone that water quality of seawater is measured (i.e., in case of missing). In the following description, although the primary scattering intensity is premised in case of just received power if not otherwise specified, the present invention can be likewise achieved when an average value of noise values is used in place of the primary scattering intensity as the received power in the measurement time zone for the measurement of water quality of seawater.

As described above, an average value of noise values is used when the primary scattering of the received power is missing in the measurement time zone for the measurement of water quality of seawater, namely, when the measurement is impossible since the primary scattering intensity is not greater than the noise values in particular. Further, in this case, as the average value of the noise values, a value calculated as an average value of the received power excluding a peak portion (a black inverted triangular symbol in FIG. 3) that appears around 0 Hz and a portion around the primary scattering is used. It is to be noted that the average value of the received power excluding the peak portion around 0 Hz and the portion around the primary scattering is defined as a noise floor. It has been confirmed that this value varies depending on each time zone (Takumi Yoshii, et al.: Discussion about Factor Affecting Data Acquisition Ratio in DBF Marine Radar Using VHF band, Hydraulic Engineering Collected Papers, Volume No. 52, 2008; and Takumi Yoshii, et al.: Discussion about Factor Affecting Data Acquisition in VHF Band DBF Marine radar, Research Paper of Central Research Institute of Electric Power Industry, V07017, 2008).

(2) Primary Scattering Intensity

The electric wave in a frequency band used by the marine radar is propagated as a surface wave or a spatial wave. The surface wave corresponds to a mode of propagating an electric wave near a land surface or a water surface. The spatial wave corresponds to a mode of reflecting an electric wave by an ionization layer, and observation in a wider range of several hundred km or above is enabled. The present invention is intended for the surface wave used by a regular marine radar and not for the spatial wave.

It is assumed that electrical characteristics of atmosphere and seawater in a marine zone as a target of water quality observation/measurement (which will be referred to as an observation marine area hereinafter) are uniform, and an electric wave is propagated on the water surface in the surface wave mode. In this case, when transmitted power is $P_t$, received power $S_{rec}$ of the marine radar obtained by an electric wave scattered at a position apart from an observing station a distance R is represented by Expression 1. Here, an attenuation coefficient A indicates a degree of propagation loss of the electric wave. It is to be noted that the propagation loss means electric energy which is lost while an electric wave reciprocates between a transmitting/receiving station and the scattering position. Further, a scattering cross section means a value representing a degree of scattering of the transmitted electric wave on the sea surface.

$$S_{rec} = \frac{P_t G_t B_{surface} A_{rec}}{(4\pi)^2 R^3} A^4 \quad \text{[Expression 1]}$$

where $B_{surface}$: a scattering cross section;
$A_{rec}$: a receiving cross section of the radar;
$G_t$: gain of a radar antenna; and
A: an attenuation coefficient.

Meanwhile, since the transmitted power $P_t$, the receiving cross section $A_{rec}$ of the radar, and the gain $G_t$ of the radar antenna do not vary with time, they are processed as constants. Therefore, factors that change the received power $S_{rec}$ is a change in the scattering cross section $B_{surface}$ and a change in the attenuation coefficient A.

(2-1) Scattering Cross Section

A primary scattering cross section B that causes the primary scattering in Expression 1 is represented by Expression 2 (Barrick, D. E.: First-order theory and analysis of MF/HF/VHF scatter from the sea, IEEE Transactions on Antennas and Propagation, vol. AP-20, pp. 2-10, 1972).

$$B(\omega_D) = 2^6 \pi k_0^2 \sum_{m=\pm 1} S(-2m\vec{k}_0)\delta(\omega_D - m\omega_B) \quad \text{[Expression 2]}$$

where S: an ocean wave spectrum;
$k_0$: a wave number of an electric wave;
$\vec{k}_0$: a wave number vector of an electric wave;
$\omega_B$: an angular velocity of a wave that causes Bragg scattering
$\omega_D$: a Doppler angular velocity; and
δ: a delta function.

S ($\pm 2m\vec{k}_0$) in Expression 2 means that the primary scattering cross section B is proportionate to an ocean wave spectrum of a sea surface wave having a wave number that is double a transmitted electric wave progressing or retrogressing in the same direction as the electric wave. In the present invention, the ocean wave having the wave number that is double the transmitted electric wave will be referred to as an observation target wave.

Since Expression 2 is an expression derived on the assumption that the sea surface is a perfect conductor, actual electrical characteristics of the seawater are not reflected in the expression. A result obtained by the present inventors suggests a possibility that the scattering cross section may be changed due to salinity in the sea water, and its influence may be possibly in the same range as later-described propagation loss (Takumi Yoshii and Others: Influence of Surface Layer Salinity in Marine Radar Observation, Research Paper of Central Research Institute of Electric Power Industry, V09003, 2009). The primary scattering cross section B when the sea surface is assumed as a general conductor is presented by Expression 3 (Toshio Iguchi: Shortwave Marine Radar 2. Principle of Shortwave Marine Radar, Review of the Communications Research Laboratory, Vol. 37, No. 3, pp. 345-360, 1991):

$$B(\omega_D) = 2^6 \pi k_0^2 \cos^2\theta \left| \frac{(\kappa-1)\{\kappa\sin^2\theta + (\kappa-\sin^2\theta)\}}{\left(\kappa\cos\theta + \sqrt{\kappa-\sin^2\theta}\right)^2} \right| \times \sum_{m=\pm 1} S(-2m\vec{k}_0)\delta(\omega_D - m\omega_B)$$ [Expression 3]

where θ: an incidence angle of an electric wave with respect to the sea surface with reference to a perpendicular for the sea surface; and κ: a complex relative dielectric constant of a lower medium.

It is to be noted that the incidence angle θ with respect to the sea surface is approximately 90 degrees in case of a surface wave.

The complex relative dielectric constant κ of the lower medium in Expression 3 is derived by Expression 4:

$$\kappa = \varepsilon^* - j\frac{\sigma}{\omega\varepsilon_0}$$ [Expression 4]

where $\varepsilon^*$: a relative dielectric constant;

ω: an angular frequency of an electric wave;

σ: electrical conductivity of a medium that scatters an electric wave;

$\varepsilon_0$: a dielectric constant in vacuum; and j: an imaginary unit.

It is to be noted that $\omega=2\pi f$ (f: a frequency of a transmitted electric wave) is achieved.

It is obvious from Expression 3 and Expression 4 that the electrical characteristics of the scattering medium affects the primary scattering cross section. However, since the incidence angle θ=90 degrees is a singular point in Expression 3, this expression cannot be applied to calculation of the primary scattering cross section B in the surface wave.

(2-2) Propagation Loss

The propagation loss of the electric wave will now be described. Specifically, the attenuation coefficient A indicative of a degree of propagation loss in Expression 1 will be explained.

An attenuation coefficient of an electric wave propagated in air in the surface wave mode greatly varies depending on electrical conductivity and a dielectric constant of the lower medium. When a formula of Knight and Robson (Knight, P. and J. Robson: Empirical Formula for Groundwave Field-Strength Calculation, Electronics Letters, vol. 20, No. 18, pp. 740-742, 1984) obtained by modifying a compensation formula of Norton so as to be applied to a broad range of phase constants is used for the attenuation coefficient A, the attenuation coefficient A is represented by Expression 5.

$$A = A_0 - (A_0 - A_{90})\sin(b)$$ [Expression 5]

where $$A_0 = \frac{2 + 0.33p}{2 + p + 0.6p^2}$$

$$A_{90} = \frac{2 + 170p}{2 + 210p + 310p^2}$$

$$b = \tan^{-1}\left[\frac{(\varepsilon+1)}{60\sigma\lambda}\right]$$

$$p = \frac{\pi R}{\lambda} \frac{1}{\sqrt{(\varepsilon+1)^2 + (60\sigma\lambda)^2}}$$

where λ: an electric wave wavelength;

R: a distance from the observing station;

σ: electrical conductivity of a lower medium in a propagation path; and $\varepsilon$: a dielectric constant of the lower medium in the propagation path.

The dielectric constant $\varepsilon$ in water hardly varies irrespective of water quality. Therefore, what affects a value of the attenuation coefficient A is a change in the electrical conductivity σ alone.

FIG. 4 shows a change in received power $S_{rec}$ calculated based on Expression 1 and Expression 5 in case of an electric wave wavelength of 12.2 m (an electric wave frequency: 25 MHz) and an electric wave wavelength of 7.2 m (an electric wave frequency: 41.9 MHz) generally used by the marine radar. It is to be noted that the received power shown in FIG. 4 is normalized by using received power at a point apart from the observing station a distance R=1 km when the electrical conductivity σ=4 Sm$^{-1}$. Furthermore, the received power in FIG. 4 is represented by a unit of decibel (dB), and the electrical conductivity is represented by a unit of Sm$^{-1}$.

It can be observed from FIG. 4 that the received power $S_{rec}$ tends to decrease in accordance with the distance R from the observing station. This is the propagation loss of the electric wave, and its degree of reduction increases as the electrical conductivity decreases. Moreover, it is known that, when a distance from the observing station is approximately 10 km or above, a change in received power due to a variation in electrical conductivity becomes a substantially fixed value (i.e., an inclination in the graph is substantially the same) irrespective of the distance. This tendency is observed in electric waves in a shortwave band in common.

(3) Summary of Information as Theoretical Base of Present Invention

Based on the above-described examination conducted by the present inventors, the following matter is known as the theoretical base of the present invention. First, the received power in the marine radar observation is represented by two functions, i.e., the scattering cross section and the propagation loss. The former is expressed as a function of an ocean wave spectrum and electrical conductivity of an observation target wave at the scattering position, and the latter serves as a function of electrical conductivity of seawater in the propagation path.

(4) Basic Concept of Estimation of Electrical Conductivity in Present Invention

Description will now be given as to a method of estimating the electrical conductivity from the received power of the marine radar by utilizing the effect of the electrical conductivity in an observation marine zone on the received power of the marine radar, the method of which was newly configured by the present inventors based on the unique information obtained by the above examination. It is to be noted that a radar observing station is installed at a position sufficiently close to a shoreline, and it is assumed that the electric wave is propagated on the water surface alone. Additionally, it is assumed that a dielectric constant in the observation marine zone is $\in = 80$.

The received power RSI (an abbreviation of Receiving Signal Intensity) of the marine radar is a function of the propagation loss and the scattering on the sea surface (which is specifically the scattering cross section) of the electric wave based on Expression 1 and Expression 3. Expression 1 and Expression 3 are integrated, and the received power RSI is represented by Expression 6:

$$RSI(\sigma, R) = B_1 S(\pm 2k) X(\sigma) A(\sigma, R) \quad \text{(Expression 6)}$$

where S: an ocean wave spectrum;
X: a function for the scattering cross section based on the electrical conductivity;
A: a function representing attenuation during propagation; and
$B_1$: a term organizing loss of the electric waves and others caused due to a system other than the distance, the electrical conductivity, the dielectric constant, and the ocean wave spectrum.

It is to be noted that k is a wave number vector.

Further, the function A indicative of the attenuation during the propagation is obtained based on the distance R from the observing station, the electrical conductivity $\sigma$, and the dielectric constant $\in$.

When 10 log 10 on both sides of Expression 6 are taken, and the received power is organized in the unit of decibel, Expression 6 is changed to Expression 7. It is to be noted that "'" (a dash) is attached to a value in the decibel unit in Expression 7. Based on Expression 7, the received power in the decibel unit is represented as a sum of respective terms.

$$RSI'(\sigma, R) = B_1' + S'(\pm 2k) + X'(\sigma) + A'(\sigma, R) \quad \text{(Expression 7)}$$

Here, since the received power of the radar is also affected by mechanical factors such as an antenna pattern and others, accurately estimating a value of a $B_1$ term is difficult, and hence it is generally difficult to directly obtain the received power by using Expression 7.

Therefore, in the present invention, the electrical conductivity is estimated by using a difference $\Delta RSI'$ between average received power in a time zone where salinity, a water temperature, and an ocean wave spectrum are known and received power at a time that measurement was carried out. As intrinsic characteristics of this method, the $B_1$ term does not include a term concerning the electrical conductivity or the ocean wave spectrum, it can be considered that a change involved by elapse of time does not occur, and hence the $B_1$ term can be erased by taking the difference in received power between the two time points. In the following description, a time zone as a target of averaging is determined as a reference time, and obtained average received power is determined as reference power. Further, a time zone that the electrical conductivity is estimated will be referred to as a measurement time.

The difference $\Delta RSI'$ in the received power is obtained from respective pieces of received power at positions apart from the observing station the same distance in the same direction. The difference $\Delta RSI'$ in the received power is specifically represented like Expression 8:

$$\Delta RSI'(\sigma, R) = S'_1 + X'(\sigma_1) + A'(\sigma_1, R) - S'_0 - X'(\sigma_0) - A'(\sigma_0, R) \quad \text{(Expression 8)}$$

where a subscript 0: a reference time; and
a subscript 1: a measurement time.

Here, as shown in FIG. 4, a change in the received power due to a variation in the electrical conductivity is substantially fixed at a point apart from the observing station approximately 10 km or more irrespective of the distance R. Based on this fact, it is assumed that the function of the propagation loss A' can be divided like Expression 9 by using an extent of influence $A_1$ of the salinity and an extent of influence $A_2$ of the distance.

$$A'(\sigma, R) = A_1(\sigma) + A_2(R) \quad \text{(Expression 9)}$$

When Expression 9 is assigned to Expression 8 to be organized, an extent of contribution $A_2$ of the distance in the propagation loss is offset by the reference time and the measurement time, thereby obtaining Expression 10:

$$\begin{aligned}\Delta RSI'(\sigma) &= (S'_1 - S'_0) + X'(\sigma_1) + A_1(\sigma_1) - \\ &\quad X'(\sigma_0) - A_1(\sigma_0) \\ &= (S'_1 - S'_0) + (Z(\sigma_1) - Z(\sigma_0)) \\ &= \Delta S' + \Delta Z\end{aligned} \quad \text{(Expression 10)}$$

where Z: a term obtained by organizing a term X' of influence of the electrical conductivity on the scattering cross section and a term $A_1'$ of influence of the same on the propagation loss.

In Expression 10, unknown terms are a deviation $\Delta S'$ of the ocean wave spectrum term S and a deviation $\Delta Z$ of the term Z of influence of the electrical conductivity $\sigma$ on the received power. That is, to obtain the electrical conductivity $\sigma$ from the difference $\Delta RSI'$ of the received power, these terms must be calculated. Since the propagation loss $A_1$ has been already explained, the ocean wave spectrum term S' will now be described hereinafter.

(5) Influence of Water Quality (Salinity, Water Temperature) on Electrical Conductivity In case of seawater, the electrical conductivity is mainly represented as a function of salinity, a water temperature, and a pressure. Here, in the electric wave in the surface wave mode, since seawater in a surface layer alone have an affect, influence of the pressure on the electrical conductivity is small. Therefore, the effect of a change in the pressure on the electrical conductivity is ignored.

Here, a method of representing the salinity by using the electrical conductivity of the seawater (which is called practical salinity) is known. This practical salinity PS (an abbreviation of Practical Salinity) is defined by Expression 11 (Background papers and supporting data on the Practical Salinity Scale 1978, UNESCO Technical Paper of Marine Science, 1981).

$$PS = 0.008 - 0.1692 K_{15}^{0.5} + 25.3851 K_{15} + 14.0941 K_{15}^{1.5} - 7.0261 K_{15}^{2} + 2.7081 K_{15}^{2.5} \quad \text{(Expression 11)}$$

where $K_{15}$: a ratio $EC_{15}/EC_k$ of electrical conductivity $EC_{15}$ when seawater is set to have a water temperature of 15° C. and 1 atmosphere with respect to electrical conductivity $EC_k$ of a standard solution of a potassium chloride measured in the same state, i.e., the water temperature of 15° C. and 1 atmosphere.

It is to be noted that Expression 11 can be applied in the range that the practical salinity PS is 2 to 42.

The electrical conductivity of the seawater greatly fluctuates due to the influence of salinity. It is said that fresh water has electrical conductivity of approximately 0.001 Sm$^{-1}$, and this value is 3 order lower than a value of the seawater, i.e., approximately 4 Sm$^{-1}$.

Further, the electrical conductivity σ of the seawater also changes due to a water temperature T. A relationship between them is represented by Expression 12.

$$\sigma(T) = \sigma(T_{ref})\{1 - \alpha(T - T_{ref})\} \quad \text{(Expression 12)}$$

where T: a water temperature;
  $T_{ref}$: a reference water temperature; and
  α: a temperature correction coefficient (which is generally approximately 0.01 to 0.03).

Based on Expression 11, since the electrical conductivity is a quartic function of the salinity, when the water temperature is known, the salinity is uniquely determined from the electrical conductivity. Moreover, Based on Expression 12, since the electrical conductivity is a linear function of the water temperature, if the salinity is known, the water temperature is uniquely determined from the electrical conductivity.

FIG. 5 shows a relationship between electrical conductivity $EC_k$=4 Sm$^{-1}$ when the standard solution of a potassium chloride has a water temperature of 15° C. and 1 atmosphere, electrical conductivity σ when the temperature correction coefficient α=0.02, the salinity PS, and the water temperature T. As shown in FIG. 5, when the water temperature is fixed, although a gradient of the electrical conductivity with respect to the salinity tends to increase as the water temperature rises, it does not greatly change in the range of 0° C. to 40° C. On the other hand, when the salinity is fixed, a gradient of the electrical conductivity with respect to the water temperature in the salinity range of 0 to 40 is smaller than the change of the electrical conductivity in the water temperature range of 0° C. to 40° C. Therefore, it can be considered that an estimation accuracy for the water temperature is smaller than that for the salinity. Additionally, a variation greatly varies depending on a value of the salinity. When the salinity is particularly low, since a change of the electrical conductivity with respect to the water temperature is small, estimation of the water temperature based on the electrical conductivity is difficult.

(6) Estimating Method of Salinity/Water Temperature Using Electrical Conductivity Information required for estimating the salinity and the water temperature from the electrical conductivity is electrical conductivity $EC_k$ and a temperature correction coefficient α of a standard solution of a potassium chloride measured at a water temperature of 15° C. and 1 atmosphere.

When obtaining the salinity from the electrical conductivity, furthermore, the water temperature must be known. The salinity can be obtained by using Expression 12 to convert the electrical conductivity in a marine area estimated from the marine radar into electrical conductivity $EC'_s$ at the water temperature 15° C. and assigning this electrical conductivity to Expression 11.

On the other hand, when obtaining the water temperature from the electrical conductivity, the salinity in the marine area must be known. When Expression 12 is modified and a ratio with respect to $EC_{15}$ is taken, Expression 13 concerning $K_{15}$ can be obtained. When Expression 13 is assigned to Expression 6, the water temperature is the only unknown, a surface layer water temperature can be estimated.

$$K_{15} = \frac{EC_{15}}{EC_k} = \frac{1}{EC_k} \frac{\sigma(T)}{\{1 + \alpha(T - 15)\}} \quad \text{[Expression 13]}$$

Further, when it is assumed that the salinity does not fluctuate between the reference time and the measurement time, Expression 12 can be modified to obtain Expression 14:

$$T = \frac{1}{\alpha}\left(\frac{\sigma(T) - \sigma(T_0)}{\sigma(T_0)}\right) + T_0 \quad \text{[Expression 14]}$$

where a subscript 0: a reference time; and
  a subscript 1: a measurement time.

(7) Consideration of Influence of Ocean Wave Spectrum Term

An ocean wave spectrum component alone of a sea surface wave, which advances along an eye direction that is a direction of an electric wave of the marine radar and also an observing direction and has a wavelength that is a half of a wavelength of the electric wave, contributes to the received power of the marine radar. Therefore, if an observation value of the ocean wave spectrum S is present, this value can be directly used in Expression 3. However, since the observation range of the marine radar covers a wide range of several km or above and installing a measurement equipment in the marine area is difficult, measuring the ocean wave spectrum at each point is not easy. In such a case, there is introduced a method for estimating the ocean wave spectrum by using a wind velocity that can be easily measured as compared with the ocean wave spectrum.

The ocean wave spectrum S(f, θ) in a planar two-dimensional wave place is represented by Expression 15 using a frequency spectrum S(f) and a directional distribution function G(f, θ). Furthermore, to use this Expression 15, an ocean wave as an observation target wave and a ratio with respect to a traveling direction of this wave must be estimated.

$$S(f,\theta) = S(f)G(f,\theta) \quad \text{(Expression 15)}$$

where f: a frequency of the ocean wave; and
  θ: a wave direction.

Here, since a wind velocity and a wind direction in the marine area vary from hour to hour, it is considered that the possibility that a distribution which is greatly biased in a specific direction is produced is small in regard to a directional distribution of the wave based on a change in wind direction. Further, in the examination conducted by the present inventors, it is known that a change in ocean wave spectrum when a wind velocity is reduced is far greater than influence of the directional distribution. Based on the above matters, in the present invention, as the influence of the ocean wave spectrum term on the received power, the influence of a Fourier frequency spectrum S(f) is serious and dominant as compared with the influence of the directional distribution. Therefore, in the present invention, the influence of the frequency spectrum S(f) of the ocean wave spectrum term on the received power will be considered based on the following method. It is to be noted that description will be given as to a case that the Fourier frequency spectrum S(f) alone is considered as the ocean wave spectrum term in this specification, but the influence of the directional distribution of the ocean wave spectrum term can be considered by measuring the directional distribution of the ocean wave or by using a known method concerning the directional distribution function G(f, θ) (for example, Longuet-Higgins, M. S.: Observations of the directional spectrum of sea waves using the motion of floating buoy, In Ocean Wave Spectra, pp. 11-132, 1961; Mitsuyasu, H. et al.: Observations of the directional spectrum of ocean waves using a cloverleaf buoy, Journal of Physical Oceanography, Vol. 5, pp. 750-760, 1975).

In the marine radar, a frequency band of the transmitted electric wave that allows an observation target wave to belong to wind waves is selected. Here, a Pierson-Moskowits spectrum (Pierson. W and L. Moskowits: A proposed spectral form for fully developed wind seas based on the similarity theory of s. a. kitaigorodskii, Journal of geophysical research, vol. 69, pp. 5181-5190, 1964) (which will be referred to as PM spectrum hereinafter) which has a typical spectral form of wind waves developed over infinite fetch is represented by Expression 16 as follows:

$$S(f) = \frac{\alpha_{PM} g^2}{(2\pi)^4} f^{-5} \exp\left\{-0.74\left(\frac{g}{2\pi U_{19.5} f}\right)^4\right\}$$ [Expression 16]

where f: a frequency of the ocean wave;
$\alpha_{PM}$: a constant (=8.10×10$^{-3}$);
$U_{19.5}$: a wind velocity at an altitude of 19.5 m above sea level; and
g: gravitational acceleration (=9.8 ms$^{-2}$)

When a small amplitude waves theory is used for the ocean wave and the ocean wave is assumed to be a deep-water wave, an ocean wave wavelength $L_W$ is obtained by Expression 17:

$$L_W = gT^2/2\pi$$ (Expression 17)

where $L_W$: an ocean wave wavelength;
T: an ocean wave cycle; and
g: gravitational acceleration (=9.8 ms$^{-2}$)

When the ocean wave cycle T is converted into the ocean wave wavelength $L_W$ and a wavelength of the electric wave is organized as $L_R$, Expression 18 is obtained:

$$f_b = \sqrt{\frac{g}{2\pi L_W}} = \sqrt{\frac{g}{\pi L_R}}$$ [Expression 18]

where $f_b$: a frequency of a wave that causes Bragg scattering.

In the received power, since an ocean wave spectrum of the wave that causes Bragg scattering alone is a problem, Expression 19 can be obtained by organizing Expression 16 and Expression 18:

$$S(L_R) = \frac{\alpha_{PM} g^2}{(2\pi)^4} \left(\frac{g}{\pi L_R}\right)^{-5/2} \times \exp\left\{-0.74\left(\frac{gL_R}{2\pi}\right)^2 (U_{19.5})^{-4}\right\}$$ [Expression 19]

When a unit of decibel is used and terms other than a wind velocity in the expression are organized, the ocean wave spectrum S' of the observation target wave is represented by Expression 20:

$$S' = (L_R) = B_2(L_R) - 19.0 U_{19.5}^{-4}$$ (Expression 20)

where $B_2$: a term that has no relation to a wind velocity or water quality and is determined by the electric wave wavelength $L_R$.

FIG. 6 shows acquisition of ocean wave spectrums of observation target waves at 41.9 MHz in the VHF band (an electric wave wavelength: 7.2 m) and 25 MHz in the HF band (an electric wave wavelength: 12.2 m), which are often used in the marine radar, by using Expression 20. It is to be noted that the ocean wave spectrums in the drawing are organized in the decibel unit.

As shown in FIG. 6, the ocean wave spectrum of the observation target wave is saturated when a wind velocity is not lower than approximately 3 ms$^{-1}$ in cases where the electric wave of 41.9 MHz in the VHF band is used for observation, and the ocean wave spectrum is substantially saturated when the wind velocity is not lower than 4 ms$^{-1}$ in cases where the electric wave of 25 MHz in the HF band is used for observation. Further, when the wind velocity is lower than this value, the ocean wave spectrum is precipitously reduced.

As a result, it is revealed that considering a time zone during which the wind velocity is lowered alone can suffice in regard to the influence of the ocean wave spectrum on the received power in radars of the VHF band and the HF band used as the marine radars.

For these reasons, a method for calculating electrical conductivity of seawater by using a relative difference (i.e., a value obtained by subtracting received power at the reference time at which salinity and a water temperature are known from received power in the measurement time) of the received power of the marine radar is verified with theoretical knowledge, and usefulness of considering influence of reduction in a Fourier spectrum of the ocean wave when the wind velocity $U_{19.5}$ is not greater than approximately 3 ms$^{-1}$ is verified in regard to the ocean wave spectrum term used in the calculating method.

Therefore, according to the water quality measuring method, the water quality measuring device, and the water quality measuring program for marine surface layers defined in claims 1 to 9, the electrical conductivity is calculated based on a relationship between a difference in received power observed by the marine radar, a change in influence of the ocean wave on the received power (in other words, a deviation in ocean wave spectrum), and a deviation in influence of the electrical conductivity on the received power, and salinity or a water temperature in an observation marine zone is estimated by using the electrical conductivity.

Furthermore, according to the water quality measuring method, the water quality measuring device, and the water quality measuring program for marine surface layers defined in claims 10 to 12, a noise floor which is an average values of noise values of the received power is used as the received power to estimate salinity in the observation marine zone. Here, since the noise floor is the average value excluding a peak portion of the received power near 0 Hz and a portion around the primary scattering, and the salinity in the marine area can be considered to be lower than salinity estimated by using the noise floor as the received power. Therefore, in case of the water quality measuring method, the water quality measuring device, and the water quality measuring program for marine surface layers defined in claims 10 to 12, a maximum value of the salinity in the observation marine area is estimated.

Advantageous Effects of Invention

According to the water quality measuring method, the water quality measuring device, and the water quality measuring program for marine surface layers of the present invention, since electrical conductivity can be calculated with use of received power observed by the marine radar and salinity or a water temperature of seawater in an observation marine area can be estimated by using the electrical conductivity, a radar obtained by the marine radar can be effectively utilized, time or a cost required for measurement of salinity or a water temperature of seawater intended for a marine area in the range of tens of km can be reduced.

DESCRIPTION OF EMBODIMENTS

Figure 1:
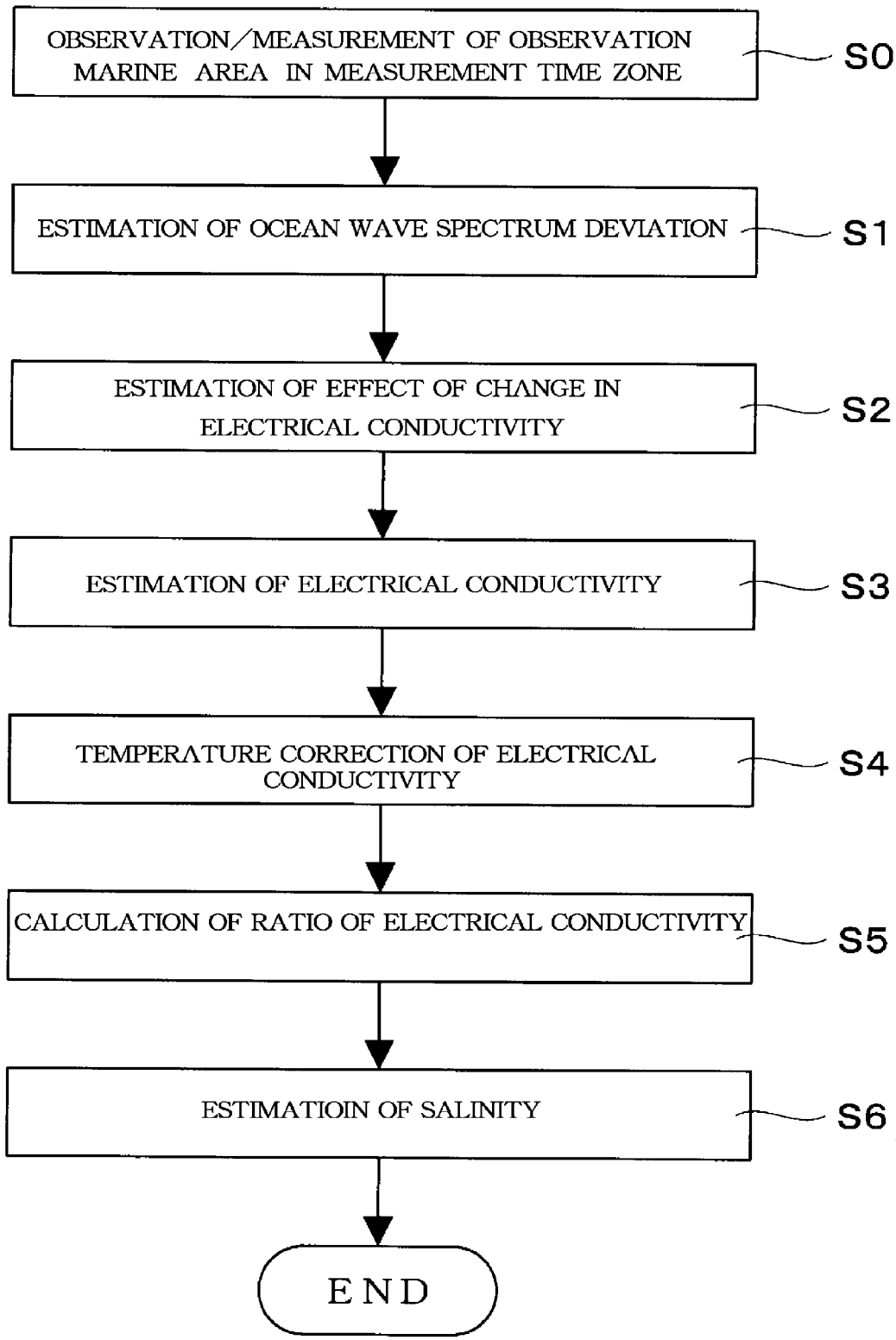
FIG. 1 is a flowchart for explaining a salinity measuring method for a marine surface layer according to a first embodiment.

A configuration of the present invention will now be described hereinafter in detail with reference to embodiments shown in the drawings.

Figure 2:
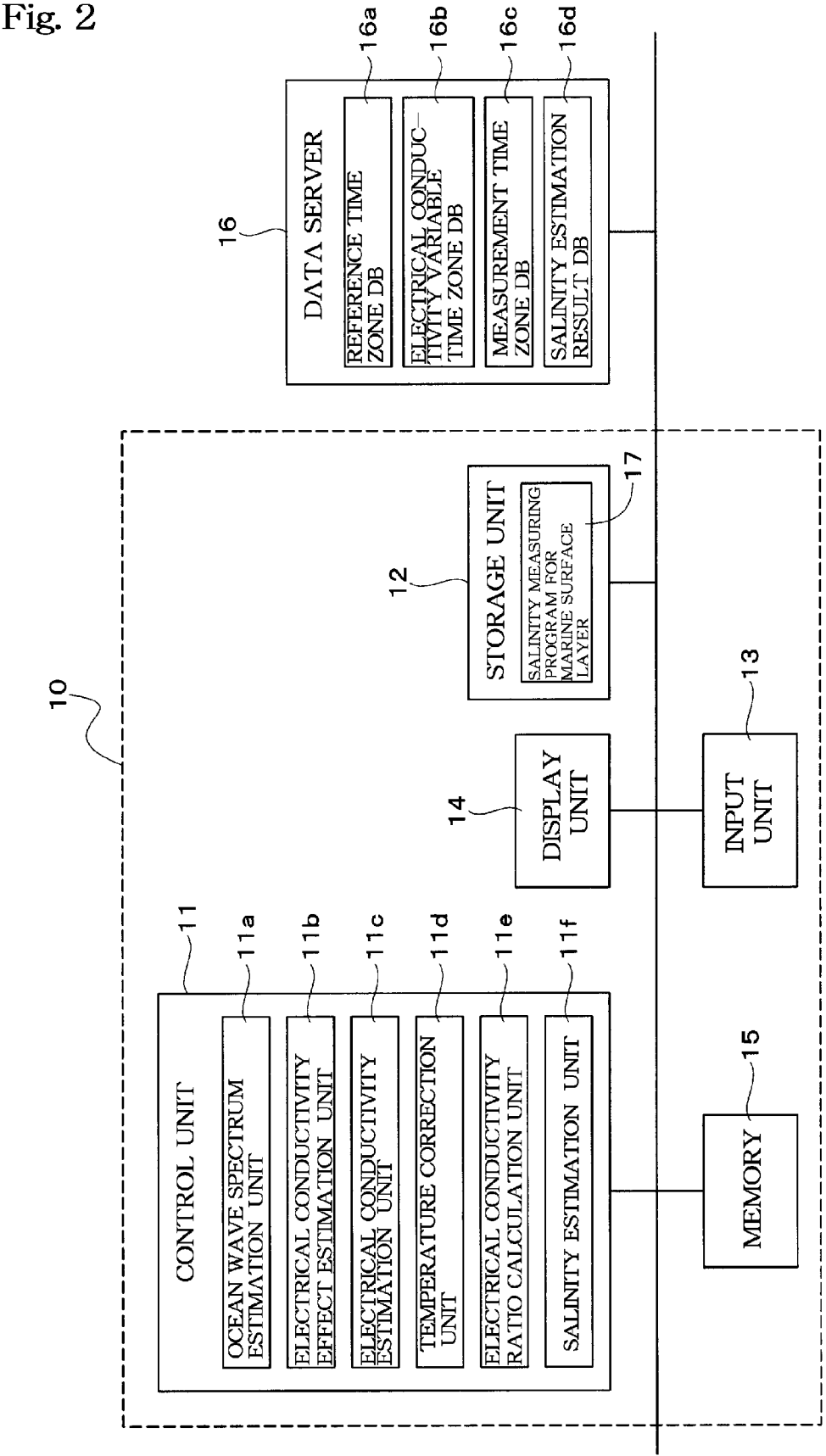
FIG. 2 is a functional block diagram of a water quality measuring device when carrying out the salinity measuring method for a marine surface layer according to the first embodiment by using a program.
Figure 3:
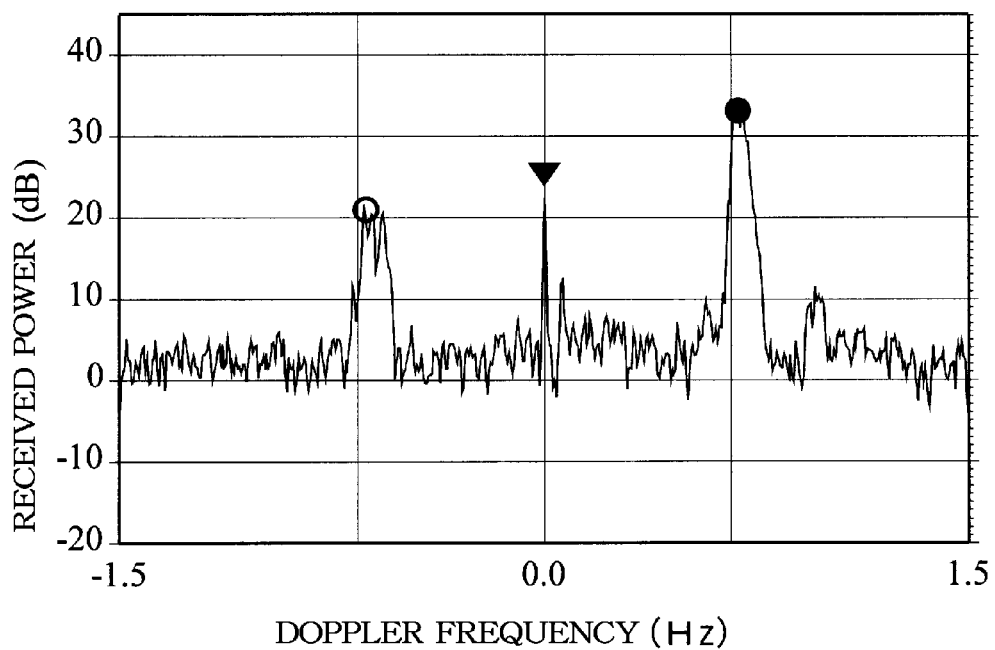
FIG. 3 is a view showing an example of a received electric wave observed by a marine radar.
Figure 4:
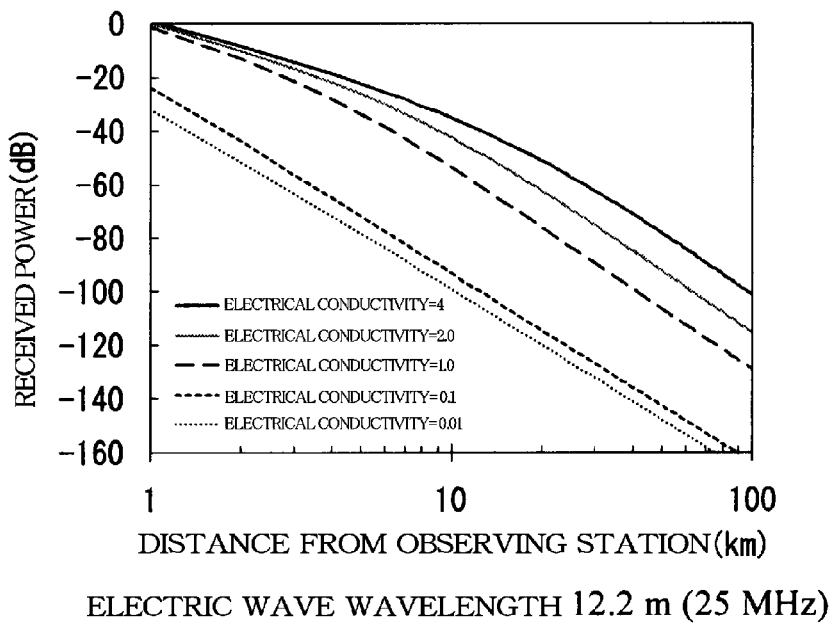
FIG. 4 is a view for explaining a tendency of received power to change based on a difference in electrical conductivity and a change in distance from an observing station.
Figure 4:
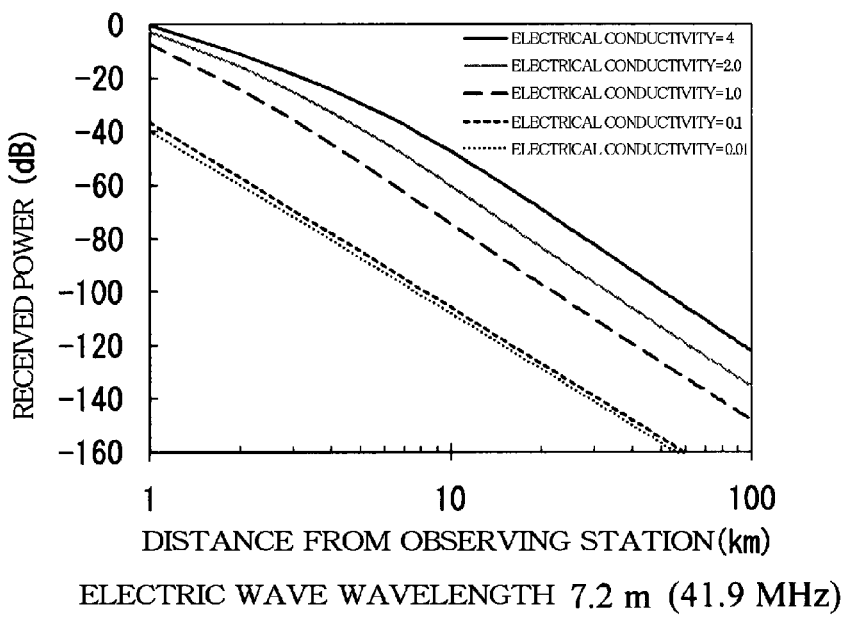

FIG. 1 and FIG. 2 show an example of a water quality measuring method, a water quality measuring device, and a water quality measuring program for marine surface layers according to a first embodiment of the present invention when measuring salinity in a marine surface layer. As shown in FIG. 1, the salinity measuring method for marine surface layers according to this embodiment comprises: a step (S1) of estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; a step (S2) of estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies and of estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; a step (S3) of estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); a step (S4) of calculating electrical conductivity $\sigma(15)$ when a water temperature is 15° C. by using the value of the electrical conductivity $\sigma_c$ in the measurement time zone; a step (S5) of calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and a step (S6) of calculating practical salinity by using the value of the ratio $K_{15}$ of the electrical conductivity.

The salinity measuring method for marine surface layers is realized as a salinity measuring device for marine surface layers. The salinity measuring device according to this embodiment comprises: means for estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies and of estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity σ(15) of the seawater to electrical conductivity of a standard solution of a potassium chloride in a standard state of 15° C. and 1 atmosphere by using the electrical conductivity σ(15) when the water temperature is 15° C.; and means for calculating practical salinity by using the value of the ratio $K_{15}$ of the electrical conductivity.

The salinity measuring device for marine surface layers is also realized by executing a salinity measuring program for marine surface layers in a computer. In this embodiment, an example that the salinity measuring program for marine surface layers is executed in a computer will be explained.

FIG. 2 shows an overall structure of a water quality measuring device 10 as a salinity measuring device according to this embodiment configured to execute a salinity measuring program 17 for marine surface layers. This water quality measuring device 10 includes a control unit 11, a storage unit 12, an input unit 13, a display unit 14, and a memory 15, and these units are connected to each other through a signal line such as a bus. Further, a data server 16 is connected to the water quality measuring device 10 through a signal line such as a bus, and signals of, e.g., data or control commands are transmitted/received (i.e., input/output) between these units through the signal line.

The control unit 11 is configured to control over the entire water quality measuring device 10 and execute arithmetic operations concerning measurement of water quality by using the salinity measuring program 17 for marine surface layers stored in the storage unit 12, and it is, e.g., a CPU (i.e., a central processing unit). The storage unit 12 is storing means capable of storing at least data or programs, and it is, e.g., a hard disk. The memory 15 serves as a memory space as a work area when executing various kinds of control or arithmetic operations by the control unit 11, and it is, e.g., a RAM (which is an abbreviation of Random Access Memory).

The input unit 13 is an interface configured to supply at least a command from an operator to the control unit 11, and it is, e.g., a keyboard.

The display unit 14 is configured to draw/display characters, figures, and others under control of the control unit 11, and it is, e.g., a display.

Moreover, the control unit 11 of the water quality measuring device 10 includes: an ocean wave spectrum estimation unit 11a as means for estimating a deviation ΔS' between the effect of an ocean wave on received power $RSI_0$' observed the marine radar in a reference time zone that electrical conductivity of seawater does not change and the effect of the ocean wave in a measurement time zone on the received power $RSI_m$' by using data of the ocean wave or a wind velocity in the reference time zone and data of the ocean waves and the wind velocity in the measurement time zone that water quality of seawater is measured; an electrical conductivity effect estimation unit 11b as means for estimating a deviation Δs' between the effect of the ocean wave on the received power $RSI_0$' in the reference time zone and the effect of the ocean wave on the received power in an electrical conductivity variable time zone by using data of the ocean wave or a wind velocity in the reference time zone and data of the ocean wave or the wind velocity in the electrical conductivity variable time zone and for estimating a regression function f(σ) of a relationship between received power obtained by subtracting the deviation Δs' from the received power observed by the marine radar in the electrical conductivity variable time zone and electrical conductivity σ in the electrical conductivity variable time zone; an electrical conductivity estimation unit 11c as means for estimating a value of electrical conductivity $σ_c$ in the measurement time zone by using $RSI_0$'−$RSI_m$'=ΔS'+{f($σ_0$)−f($σ_c$)} (where $σ_c$: electrical conductivity in the reference time zone); a temperature correction unit 11d as means for calculating electrical conductivity σ(15) when a water temperature is 15° C. by using the value of the electrical conductivity $σ_c$ in the measurement time zone; an electrical conductivity ratio calculation unit 11e as means for calculating a ratio $K_{15}$ of the electrical conductivity σ(15) of the seawater to electrical conductivity of a standard solution of a potassium chloride in a standard state of 15° C. and 1 atmosphere by using the electrical conductivity σ(15) when the water temperature is 15° C.; and a salinity estimation unit 11f as means for calculating practical salinity by using a value of the ratio $K_{15}$ of the electrical conductivity.

When carrying out this embodiment, observation/measurement is conducted in an observation marine area in advance, and marine radar received power, electrical conductivity (fixed without varying in a corresponding time zone), and an ocean wave or a wind velocity in a time zone that the electrical conductivity does not vary (in other words, it is fixed at each point) and an observation target wave has been sufficiently developed (in other words, a time zone that the wind velocity in the observation marine area is sufficiently obtained) are prepared as combination data of results of conducting the observation/measurement at the same time. It is to be noted that the time zone that the observation/measurement is conducted in advance when carrying out this embodiment, which is also a time zone that the electrical conductivity does not vary and the observation target wave has been sufficiently developed, will be referred to as the reference time zone in the present invention.

In the present invention, the received power is observed by the same method as a conventional method for observing a surface layer current in the marine area by using the marine radar. Specifically, for example, a marine radar having one transmitting antenna and a plurality of receiving antennas is installed in a coast of the observation marine area, and electrical waves are periodically transmitted/received to perform the observation.

The same method as the conventional method is also used for a method of transmitting/receiving electrical waves in the observation using the marine radar or division of the received electric waves into a plurality of directions. It is to be noted that each direction to which the received electric wave is divided is an observing direction of the marine radar, and it is also an eye direction.

Figure 5:
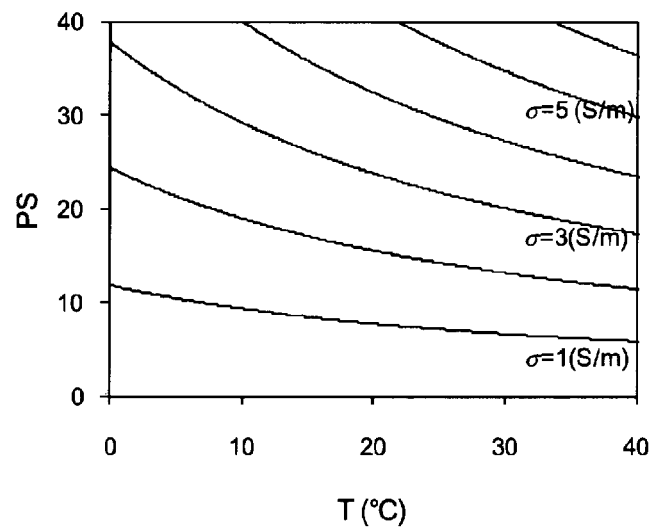
FIG. 5 is a view for explaining a relationship between a water temperature, salinity, and electrical conductivity.
Figure 6:
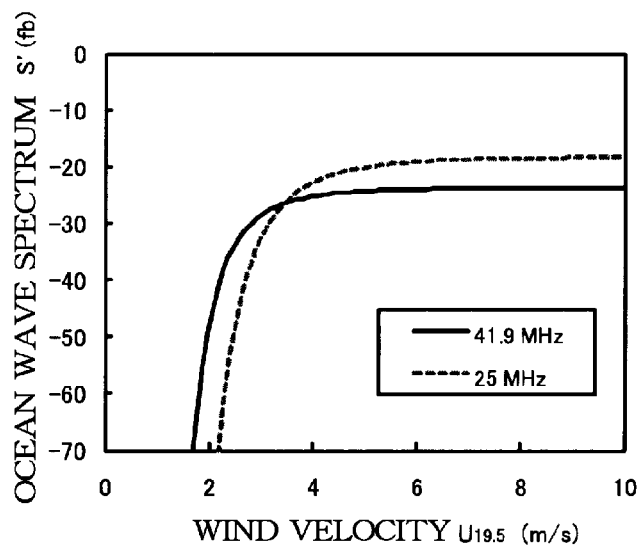
FIG. 6 is a view showing a change in ocean wave spectrum involved by a change in wind velocity in accordance with each electric wave wavelength.

Further, in the present invention, the electrical conductivity may be directly measured by, e.g., a CTD (an abbreviation of Conductivity-Temperature-Depth profiler) in the observation marine area, or it may be determined by measuring a water temperature and practical salinity PS and using a relationship shown in FIG. 5.

It is desirable to perform the measurement of the electrical conductivity in the present invention in the eye direction of the marine radar that observes the observation marine area or at a point near the eye direction.

Furthermore, the measurement of the ocean wave in the present invention is performed by any one of various kinds of conventionally adopted measuring methods that can measure an ocean wave spectrum. Moreover, the measurement of the wind velocity in the present invention is effected by setting up a conventionally adopted anemometer. A measurement height of the wind velocity is not restricted to a specific height if it is fixed during the measuring, and it may be 19.5 m from the ground or any other height.

It is desirable to measure the ocean wave or the wind velocity in the present invention in the eye direction of the marine radar that observes the observation marine area or at a point near the eye direction. Additionally, it is desirable for the measurement of the ocean wave or the wind velocity to avoid a point that has a special tendency mainly in regard to increase/decrease of the ocean wave or the wind velocity due to the effect of the observation marine area or its surrounding landform as compared with a normal situation in the observation marine area.

It is desirable to carry out the measurement of the electrical conductivity and the ocean wave or the wind velocity in the reference time zone at a plurality of points in the observation marine area or its periphery, and it is preferable to perform the measurement of both the values at the same point or points close to each other.

When carrying out this embodiment, further, the observation/measurement is conducted in the observation marine area in advance, thereby the marine radar received power, the electrical conductivity, and an ocean wave or the wind velocity are prepared as combination data of results of conducting the observation/measurement at the same time in a time zone that the electrical conductivity varies. It is to be noted that a time zone that the observation/measurement is conducted in advance when carrying out this embodiment, which is also the time zone that the electrical conductivity varies, will be referred to as the electrical conductivity variable time zone.

In regard to the observation of the received power using the marine radar, it is desirable to install an observation device of the marine radar at the same point and perform observation in the same eye direction for observation in the reference time zone and observation in the electrical conductivity variable time zone.

It is desirable to conduct the measurement of the electrical conductivity and the ocean wave or the wind velocity in the electrical conductivity variable time zone at the same point or points close to each other, and it is preferable to conduct this measurement at the same point as or a point close to the measurement point for the electrical conductivity and the ocean wave or the wind velocity in the reference time zone.

Further, in this embodiment, data obtained by the observation/measurement in the reference time zone is stored in the data server 16 as a reference time zone database 16*a* in the form of combination data of a value of the received power, a value of the electrical conductivity, a value of the ocean wave (which is specifically an ocean wave spectrum) or the wind velocity in association with information of the observation/measurement time. It is to be noted that information of the eye direction and a distance is further associated with the data of the received power. Furthermore, as information of a measurement position, information of an eye direction which is the closest to these measurement points and a distance from the marine radar is further associated with the data of the electrical conductivity and the data of the ocean wave or the wind velocity.

In this embodiment, moreover, data obtained by the observation/measurement in the electrical conductivity variable time zone is stored as combination data of a value of the received power, a value of the electrical conductivity, and a value of the ocean wave (which is specifically an ocean wave spectrum) or the wind velocity in the data server 16 as an electrical conductivity variable time zone database 16*b* in association with the information of the observation/measurement time. It is to be noted that the information of the eye direction and the distance is further associated with the data of the received power. Additionally, as the information of the measurement position, the information of an eye direction which is the closest to these measurement points and a distance from the marine radar is further associated with the data of the electrical conductivity and the data of the ocean wave or the wind velocity.

After the preparation of the data concerning the reference time zone and the preparation of the data concerning the electrical conductivity variable time zone in regard to the observation marine area, water quality is measured in the observation marine area. It is to be noted that a time during which the water quality is measured (in other words, a time as a measurement target) will be referred to as a measurement time zone in the present invention. Further, the database will be referred to as a DB hereinafter.

When executing processing according to this embodiment concerning the measurement time zone, observation of the received power using the marine radar, measurement of the ocean wave or the wind velocity, and measurement of a water temperature are first performed in the observation marine area (S0).

As to the observation of the received power using the marine radar, it is preferable to install the observation device of the marine radar at the same point for the observation in the reference time zone and the observation in the measurement time zone and to observe in the same eye direction, and the same electric wave wavelength is used.

Further, the measurement of the ocean wave or the wind velocity in the observation marine area and the above observation of the received power are carried out at the same time. As to the measurement of the wind velocity, a measurement height for the measurement in the reference time zone is set to be equal to a measurement height for the measurement in the measurement time zone.

It is desirable to measure the ocean wave or the wind velocity in the measurement time zone at a plurality of points in the observation marine area or its periphery, and it is preferable to perform this measurement at a point equal to or a point close to the measurement point of the ocean wave or the wind velocity in the reference time zone or the electrical conductivity variable time zone.

Moreover, the water temperature in the observation marine area is measured at the same time. In regard to the measurement of a water temperature, a conventionally adopted water temperature gauge is installed to measure the water temperature in the marine surface layer.

It is desirable to measure the water temperature in the measurement time zone in the eye direction of the marine radar that observes the observation marine area or at a point close to the eye direction, carry out this measurement of the water temperature at a plurality of points in the observation marine area, and effect this measurement at a point equal to or close to the measurement point for the ocean wave or the wind velocity in the reference time zone, the electrical conductivity variable time zone, or the measurement time zone.

Additionally, the observation of the received power, the measurement of the ocean wave or the wind velocity, and the measurement of the water temperature in the observation marine area are carried out at the same observation/measurement time both in a situation that these types of measurement are continuously performed and a situation that they are carried out at fixed intervals.

In this embodiment, data obtained by the observation/measurement in the measurement time zone is associated with information of the observation/measurement to be stored as combination data of a value of the received power, a value of the ocean wave (which is specifically an ocean wave spectrum) or the wind velocity, and a value of the water temperature in the data server 16 as a measurement time zone DB 16*c*. It is to be noted that information of the eye direction and the distance is further associated with the data of the received power. As information of the measurement position, information of an eye direction which is the closest to these measurement points and a distance from the marine radar is further associated with the data of the ocean wave or the wind velocity and the data of the water temperature.

Furthermore, in this embodiment, the following processing of S1 to S6 is executed by using data in the reference time zone prepared in the reference time zone DB 16a, data in the electrical conductivity variable time zone prepared in the electrical conductivity variable time zone DB 16b, and data in the measurement time zone stored in the measurement time zone DB 16c.

First, the ocean wave spectrum estimation unit 11a of the control unit 11 estimates a deviation between the effect of the ocean wave on the received power of the marine radar in the reference time zone and the effect of the ocean wave on the received power in the measurement time zone, i.e., a deviation between ocean wave spectra (S1).

The deviation between the ocean wave spectra in the present invention is calculated using data of the ocean wave spectra when the ocean waves are measured to obtain the ocean wave spectra in the reference time zone and the measurement time zone, or this deviation is calculated using data of wind velocities when the wind velocities are measured in place of the ocean waves in both the time zones.

(1) When Ocean Waves have been Measured:

First, when the ocean waves have been measured to obtain the ocean wave spectra, specifically, the ocean wave spectrum estimation unit 11a reads time-specific ocean wave spectra in the reference time zone from the reference time zone DB 16a stored in the data server 16 and calculates an average $S_0'$ of the ocean wave spectra in the reference time zone by using the time-specific ocean wave spectra.

The ocean wave spectrum estimation unit 11a further reads an ocean wave spectrum $S_1'$ in the measurement time zone from the measurement time zone DB 16c stored in the data server 16 and calculates $S_0'-S_1'$ to obtain a deviation ocean wave spectrum $\Delta S'$ in the measurement time zone.

The calculation of $S_0'-S_1'$ is executed in accordance with each date and hour in the measurement time zone for each data of the ocean waves recorded in the measurement time zone DB 16c (in other words, the calculation is executed in accordance with each eye direction associated with each ocean wave data and with each distance from the marine radar). That is, one value applied to the entire observation marine area (i.e., to every point) in common is calculated when the ocean wave measurement is performed at one point alone in the observation marine area, or this calculation is executed for each point when the ocean wave measurement is performed at a plurality of points. It is to be noted that, when measurement points in the reference time zone are different from those in the measurement time zone, the respective measurement points in both the time zones are compared to and associated with each other, the observation marine area is appropriately divided, and the calculation of $S_0'-S_1'$ is carried out in accordance with each divided area.

Further, the ocean wave spectrum estimation unit 11a stores the calculated value of the deviation ocean wave spectrum $\Delta S'$ in the memory 15 in association with information of a date and hour, an eye direction which is the closest to a point or a region where $\Delta S'$ is calculated, and a distance from the marine radar.

(2) When Wind Velocities have been Measured:

Subsequently, when wind velocities have been measured, a deviation of received power due to a change in ocean wave spectra is calculated by using the wind velocities. In the present invention, there are the two following methods for estimating a deviation between the effect of an ocean wave spectrum on received power of the marine radar in the reference time zone and the effect of an ocean wave spectrum on the received power in the measurement time by using the wind velocities.

2-1) Method Using Expression 20

The ocean wave spectrum estimation unit 11a first assigns an electric wave wavelength $L_R$ of the marine radar used for observation in the reference time zone and a wind velocity $U_{19.5}$ measured in the observation marine area in the reference time zone to Expression 20 to estimate an ocean wave spectrum $S'(L_R)$.

For example, a data file having various kinds of set values used for processing of S1 to S6 defined therein may be stored in the storage unit 12, and a value of the electric wave wavelength $L_R$ of the marine radar may be defined in the data file so that the ocean wave spectrum estimation unit 11a can read this value from the data file, or a message having contents for requesting specification of a value of the electric wave wavelength $L_R$ may be displayed in the display unit 14 at the time of processing of S1, and the ocean wave spectrum estimation unit 11a may read a value specified by an operator and input through the input unit 13.

Furthermore, the ocean wave spectrum estimation unit 11a reads a value of the time-specific wind velocity $U_{19.5}$ from the reference time zone DB 16a stored in the data server 16 and assigns this value to Expression 20 to estimate the time-specific ocean wave spectrum $S'(L_R)$ in the reference time zone.

The ocean wave spectrum estimation unit 11a further calculates an average $S_0'(L_R)$ of the ocean wave spectra in the reference time zone using each time-specific ocean wave spectrum $S'(L_R)$ estimated in the above-described processing.

Furthermore, the ocean wave spectrum estimation unit 11a stores a value of the average $S_0'(L_R)$ of the ocean wave spectra in the reference time zone in the memory 15 as a reference time ocean wave spectrum $S_0'(L_R)$.

Moreover, the ocean wave spectrum estimation unit 11a assigns the electric wave wavelength $L_R$ of the marine radar used for the observation in the measurement time zone and the wind velocity $U_{19.5}$ measured in the observation marine area in the measurement time zone to Expression 20 to estimate an ocean wave spectrum $S_1'(L_R)$.

Specifically, the ocean wave spectrum estimation unit 11a reads a value of the electric wave wavelength $L_R$ of the marine radar in the same manner as described above, also reads a value of the wind velocity $U_{19.5}$ from the measurement time zone DB 16c stored in the data server 16, and assigns these values to Expression 20 to estimate the ocean wave spectrum $S_1'(L_R)$ in the measurement time zone.

Additionally, the ocean wave spectrum estimation unit 11a reads a values of the reference time ocean wave spectrum $S_0'(L_R)$ stored in the memory 15 in the above-described processing and calculates $S_0'(L_R)-S_1'(L_R)$ to obtain the deviation ocean wave spectrum $\Delta S'$ in the measurement time zone.

Processing concerning the calculation of the deviation ocean wave spectrum $\Delta S'$ is executed for each wind velocity data recorded in the measurement time zone DB 16c in accordance with each date and hour in the measurement time zone (in other words, this processing is executed in accordance with each eye direction associated with the wind velocity data and with each distance from the marine radar). That is, the processing is executed to calculate one value applied to the entire observation marine area (i.e., to every point) in common when the wind velocity measurement is carried out at one point alone in the observation marine area, or this processing is executed in accordance with each point when the wind velocity measurement is carried out at a plurality of points. It is to be noted that, when measurement points in the reference time zone are different from those in the measurement time zone, the respective measurement points in both the time zones are compared to and associated with each other, the observation marine area is appropriately divided, and the calculation of $S_0'-S_1'$ is carried out in accordance with each divided area.

Additionally, the ocean wave spectrum estimation unit 11$a$ stores the calculated value of the deviation ocean wave spectrum $\Delta S'$ in the memory 15 in association with information of a date and hour, an eye direction which is the closest to a point or a region where $\Delta S'$ is calculated, and a distance from the marine radar.

2-2) Method Using Wind Velocity Regression Function

In the application of the present invention, a deviation between the effect of the ocean wave spectrum on the received power of the marine radar in the reference time zone and the effect of the ocean wave spectrum on the received power in the measurement time zone may be estimated, in other words, a deviation ocean wave spectrum may be estimated by the following method without using Expression 20. For example, when a wind velocity is measured at a height that is not 19.5 from the ground and a value of the wind velocity $U_{19.5}$ in the reference time zone or the measurement time zone is not prepared, the following method is effective.

When estimating the effect of the ocean wave spectrum on the received wave without using Expression 20, a regression function of a relationship between a value of the received power and a value of the wind velocity in the reference time zone is estimated, and this regression function (which will be referred to as a wind velocity regression function hereinafter) is used to estimate the effect.

A function form of a regression curve (i.e., a function form of the wind velocity regression function) when regressing the relationship between the value of the received power and the value of the wind velocity is not restricted to a specific form, and an operator can select a function form that can appropriately represent the relationship between both the values by plotting on a graph combination data of the value of the received power and the value of the wind velocity at the same clock time in the reference time zone, for example. Specifically, for example, using a logarithmic function shown in Expression 21 can be considered.

$$RSI'=a_1 \operatorname{Log}(U)+b_1 \quad \text{(Expression 21)}$$

where RSI': received power [dB],

U: a wind velocity [ms$^{-1}$], and $a_1$, $b_1$: a regression coefficient, a constant term.

The wind velocity regression function estimation processing is executed using each time-specific wind velocity in the reference time zone measured at one point in the observation marine area and received power in an eye direction/distance which is the closest to the wind velocity measurement point. It is to be noted that the operator selects a function form of the wind velocity regression function and defines this function form in the salinity measuring program 17 for marine surface layers in advance.

Here, since a fluctuation in ocean wave spectrum due to a change in wind velocity can be considered to be equal at any point in the observation marine area, the regression coefficient $a_1$ in Expression 21 is fixed when the logarithmic function shown in Expression 21 is used as the function form of the wind velocity regression function, and $a_1 \operatorname{Log}(U)$ can be applied to the entire observation marine area (i.e., to every point).

On the other hand, the constant term $b_1$ in Expression 21 corresponds to a sum of $B_1'$, $X'(\sigma)$, and $A'(\sigma, R)$ in Expression 7, and it can be considered that this term varies depending on an eye direction of the marine radar and a distance from the marine radar when electrical conductivity in the observation marine area is fixed. However, $B_1'$ and an attenuation term $A_2(R)$ based on a distance are used to calculate a difference and are thereby offset, these values do not have to be calculated. In addition, to offset $B_1'$, it is desirable to install the observation device of the marine radar at the same point in observation in the reference time zone, the electrical conductivity variable time zone, and the measurement time zone and perform the observation in the same eye direction. $Z(\sigma) (=A_1(\sigma)+X'(\sigma))$ is evaluated by a method that will be explained as processing of S2.

To execute the above-described processing, the ocean wave spectrum estimation unit 11$a$ reads combination data of a value of each time-specific received power and a value of each time-specific wind velocity at the one point from the reference time zone DB 16$a$ stored in the data server 16, estimates the regression function, i.e., the wind velocity regression function representing the relationship between the value of the received power and the value of the wind velocity, and stores a value of a regression coefficient ($a_1$ in case of Expression 21) of the estimated wind velocity regression function in the memory 15. It is to be noted that the estimation of the regression function is carried out using, e.g., a least-square method.

Further, the ocean wave spectrum estimation unit 11$a$ reads a value of each time-specific wind velocity U from the reference time zone DB 16$a$, assigns this value to the wind velocity regression function to estimate each time-specific received power RSI' (which is a value excluding that of the constant term) in the reference time zone, and uses each time-specific received power RSI' to calculate an average $RSI_0'$ (which is a value excluding that of the constant term) of the received power in the reference time zone.

Furthermore, the ocean wave spectrum estimation unit 11$a$ stores a value of the average $RSI_0'$ of the received power in the reference time zone in the memory 15 as reference time received power $RSI_0'$.

Moreover, the ocean wave spectrum estimation unit 11$a$ assigns the wind velocity U measured in the measurement time zone in the observation marine area to the wind velocity regression function to estimate received power $RSI_1'$ (which is a value excluding that of the constant term).

Specifically, the ocean wave spectrum estimation unit 11$a$ reads a value of the wind velocity U from the measurement time zone DB 16$c$ stored in the data server 16 and assigns this value to the wind velocity regression function to estimate the received power $RSI_1'$ (which is a value excluding that of the constant term) in the measurement time zone.

Additionally, the ocean wave spectrum estimation unit 11$a$ reads a value of reference time received power $RSI_0'$ stored in the memory 15 by the above-described processing and calculates $RSI_0'-RSI_1'$.

Processing concerning the calculation of $RSI_0'-RSI_1'$ using the wind velocity regression function is executed for each wind velocity data recorded in the measurement time zone DB 16$c$ in accordance with each date and hour in the measurement time zone (in other words, this processing is executed in accordance with each eye direction associated with the wind velocity data and with each distance from the marine radar). That is, the processing is executed to calculate one value applied to the entire observation marine area (i.e., to every point) in common when the wind velocity measurement is carried out at one point alone in the observation marine area, or this processing is executed in accordance with each point when the wind velocity measurement is carried out at a plurality of points. It is to be noted that, when measurement points in the reference time zone are different from those in the measurement time zone, the respective measurement points in both the time zones are compared to and associated with each other, the observation marine area is appropriately divided, and the calculation of $RSI_0'-RSI_1'$ is carried out in accordance with each divided area.

Additionally, the ocean wave spectrum estimation unit 11a stores the value of $RSI_0'-RSI_1'$ in the memory 15 as the deviation ocean wave spectrum $\Delta S'$ in the measurement time zone in association with information of a date and hour, an eye direction which is the closest to a point or a region where $\Delta S'$ is calculated, and a distance from the marine radar.

Subsequently, the electrical conductivity effect estimation unit 11b of the control unit 11 estimates the effect of a change in electrical conductivity on the received power in the measurement time zone (S2)

In regard to $Z(\sigma_1)-Z(\sigma_0)$ ($=X'(\sigma_1)+A_1(\sigma_1)-X'(\sigma_0)-A_1(\sigma_0)$) in Expression 10 which is a basic formula of a relationship between the difference $\Delta RSI'$ of the received power, the deviation of the ocean wave spectrum term S', and the deviation of the effect of the electrical conductivity on the received power, an effect term X' of the electrical conductivity on scattering intensity cannot be theoretically calculated. Therefore, in the present invention, an element corresponding to $Z(\sigma_1)-Z(\sigma_0)$ in Expression 10 is evaluated as the effect of a change in electrical conductivity on the received power.

Specifically, in the present invention, a regression function $f(\sigma)$ of a relationship between a value of the received power and a value of the electrical conductivity $\sigma$ in the electrical conductivity variable time zone is estimated, and $Z(\sigma_1)(\sigma_0)$ in Expression 10 is estimated using the regression function (which will be referred to as an electrical conductivity regression function hereinafter) $f(\sigma)$.

Here, as the value of the received power in the electrical conductivity variable time zone used for estimation of the electrical conductivity regression function $f(\sigma)$, data obtained by eliminating the effect of the ocean wave on the received power in the electrical conductivity variable time zone from a result of executing the same processing as the processing of S1 is used. Specifically, data in the reference time zone and data in the measurement time zone are used to estimate the deviation ocean wave spectrum $\Delta S'$ in the measurement time zone in the processing of S1, whereas data in the reference time zone and data in the electrical conductivity variable time zone are used to estimate the deviation ocean wave spectrum $\Delta s'$ in the electrical conductivity variable time zone and a result obtained by subtracting the deviation ocean wave spectrum $\Delta s'$ from the received power actually observed in the electrical conductivity variable time zone is used as the value of the received power in the processing of S2.

The function form of the regression curve (i.e., a function form of the electrical conductivity regression function $f(\sigma)$) when regressing the relationship between the value of the received power after subtracting the deviation ocean wave spectrum $\Delta s'$ in the electrical conductivity variable time zone and the value of the electrical conductivity is not restricted to a specific form, and an operator may select a function form that can appropriately represent the relationship between them after plotting combination data of the value of the received power and the value of the electrical conductivity at the same clock time in the electrical conductivity variable time zone, for example. Specifically, for example, using a linear function shown in Expression 22 can be considered:

$$RSI'=f(\sigma)=a_2\sigma+b_2 \qquad \text{(Expression 22)}$$

where RSI': received power [dB] (a value obtained by subtracting the deviation ocean wave spectrum from an actual observation value);

σ: electrical conductivity [$Sm^{-1}$]; and $a_2, b_2$: regression coefficient, constant term.

Estimation processing of the electrical conductivity regression function $f(\sigma)$ is executed using the time-specific electrical conductivity measured at one point in the observation marine area in the electrical conductivity variable time zone and the received power in an eye direction/distance that is the closest to the electrical conductivity measurement point. It is to be noted that the function form of the electrical conductivity regression function $f(\sigma)$ is selected by the operator and defined in the salinity measuring program 17 for marine surface layers in advance.

To execute the above processing, the electrical conductivity effect estimation unit 11b first uses data stored in the reference time zone DB 16a and the electrical conductivity variable time zone DB 16b stored in the data server 16 and estimates the deviation ocean wave spectrum $\Delta s'$ in the electrical conductivity variable time zone by the method using the ocean wave measurement data described as the processing of S1, the method of using Expression 20, or the method of using the wind velocity regression function. It is to be noted that estimation of the deviation ocean wave spectrum $\Delta s'$ in the processing of S2 may be carried out at one point in the observation marine area used for the estimation processing of the electrical conductivity regression function $f(\sigma)$.

Additionally, the electrical conductivity effect estimation unit lib stores the estimated value of the deviation ocean wave spectrum $\Delta s'$ in the electrical conductivity variable time zone in the memory 15.

Further, the electrical conductivity effect estimation unit 11b reads the time-specific combination data of the value of the received power and the value of the electrical conductivity at the one point from the electrical conductivity variable time zone DB 16b, subtracts the deviation ocean wave spectrum $\Delta s'$ in the electrical conductivity variable time zone stored in the memory 15 from the value of the received power, and stores resultant data in the memory 15 as combination data of the value of the received power and the value of the electrical conductivity used for estimation of the electrical conductivity regression function $f(\sigma)$.

Furthermore, the electrical conductivity effect estimation unit 11b reads the time-specific combination data of the value of the received power and the value of the electrical conductivity at the one point stored in the memory in the above-described processing and estimates the regression function representing the relationship between the value of the received power and the value of the electrical conductivity, i.e., the electrical conductivity regression function $f(\sigma)$. It is to be noted that the regression function is estimated by using, e.g., the least-square method.

Furthermore, the electrical conductivity effect estimation unit 11b stores the estimated values of the regression coefficient and the constant term ($a_2$ and $b_2$ in Expression 22) of the electrical conductivity regression function $f(\sigma)$ in the memory 15.

Subsequently, the electrical conductivity estimation unit 11c of the control unit 11 estimates the electrical conductivity in the measurement time zone (S3). It is to be noted that processing of S3 to S6 is executed in accordance with each date and hour in the measurement time zone and each data of the received power recorded in the measurement time zone DB 16c (in other words, the processing is executed in accordance with each eye direction of the marine radar and each distance from the marine radar).

The electrical conductivity estimation unit $11c$ reads from the memory 15 the value of the reference time received power $RSI_0'$ and the value of the deviation ocean wave spectrum $\Delta S'$ in the measurement time zone stored in the memory 15 in the processing of S1 and the values of the regression coefficient and the constant term of the electrical conductivity regression function $f(\sigma)$ stored in the memory 15 in the processing of S2, reads the value of the electrical conductivity $\sigma_0$ in the reference time zone from the reference time zone DB $16a$, and also reads the value of the received power $RSI_m'$ in the measurement time zone from the measurement time zone DB $16c$. However, the constant term of the electrical conductivity regression function may be ignored since it is canceled out to calculate a difference.

Moreover, the electrical conductivity $\sigma_0$ in the measurement time zone is estimated by using Expression 23 obtained by rewriting Expression 10.

$$RSI_0' - RSI_m' = \Delta S' + \{f(\sigma_0) - f(\sigma_c)\} \quad \text{(Expression 23)}$$

Here, information of a date and hour, an eye direction which is the closest to a point or a region where $\Delta S'$ was calculated, and a distance from the marine radar is associated with a value the deviation ocean wave spectrum $\Delta S'$ in the measurement time zone in the processing of S1, and the processing of S3 is carried out in accordance with each date and hour, each eye direction of the marine radar, and each distance from the marine radar. Therefore, a value associated with an eye direction and a distance which are the closest to an eye direction and a calculation target distance associated with a value of the received power $RSI_m'$ read from the measurement time zone DB $16c$ to estimate the electrical conductivity $\sigma_c$ for each eye direction/distance is selected from values of the deviation ocean wave spectrum $\Delta S'$ stored in the memory 15.

Further, since information of an eye direction which is the closest to a measurement point of the electrical conductivity and a distance from the marine radar is associated with a value of the electrical conductivity $\sigma_0$ in the reference time zone stored in the reference time zone DB $16a$, a value of the electrical conductivity $\sigma_0$ associated with an eye direction and a distance which are the closest to an eye direction and a calculation target distance associated with a value of the received power $RSI_m'$ is selected and used like the above.

Furthermore, the electrical conductivity estimation unit $11c$ stores the estimated value of the electrical conductivity $\sigma_c$ in the memory 15 in association with the information of a date and hour, an eye direction, and a distance from the marine radar.

Subsequently, the temperature correction unit $11d$ of the control unit 11 performs temperature correction with respect to the value of the electrical conductivity estimated in the processing of S3 (S4).

Specifically, the temperature correction unit $11d$ reads the value of the electrical conductivity $\sigma_c$ stored in the memory 15 in the processing of S3 from the memory 15 and also reads a water temperature $T_{ref}$ in the measurement time zone from the measurement time zone DB $16c$. It is to be noted that a value associated with an eye direction and a distance which are the closest to the eye direction and the distance associated with the value of the electrical conductivity $\sigma_c$ read from the memory 15 to carry out the temperature correction is selected from values of the water temperature $T_{ref}$ stored in the measurement time zone DB $16c$, and the selected value is used.

Moreover, in regard to the electrical conductivity estimated in the processing of S3, the temperature correction unit $11d$ calculates a value of electrical conductivity $\sigma(15)$ at a water temperature of 15° C. by using Expression 12. Here, in regard to variables in Expression 12, the value of the electrical conductivity $\sigma_c$ estimated in the processing of S3 is set to $\sigma(T_{ref})$, and T=15 is set. It is to be noted that Expression 12 including a value of a temperature correction coefficient $\alpha$ is defined in the salinity measuring program 17 for marine surface layers.

Further, the temperature correction unit $11d$ stores the calculated value of the electrical conductivity $\sigma(15)$ in the memory 15 in association with the information of a data and hour, an eye direction, and a distance from the marine radar.

Subsequently, the electrical conductivity ratio calculation unit $11e$ of the control unit 11 calculates a ratio of the electrical conductivity of seawater with respect to electrical conductivity of a standard solution of a potassium chloride in a standard state of 15° C. and 1 atmosphere by using the value of the electrical conductivity after the temperature correction calculated in the processing of S4 (S5).

Specifically, the electrical conductivity ratio calculation unit $11e$ reads from the memory 15 the value of the electrical conductivity $\sigma(15)$ stored in the memory 15 in the processing of S4 and assigns the read value to Expression 24 to calculate a ratio $K_{15}$ of the electrical conductivity.

$$K_{15} = \sigma(15)/\sigma_{KCl}(15) \quad \text{(Expression 24)}$$

where $\sigma_{KCl}(15)$: electrical conductivity of the standard solution of the potassium chloride in the standard state of 15° C. and 1 atmosphere.

Furthermore, the electrical conductivity ratio calculation unit $11e$ stores the calculated value of the ratio $K_{15}$ of the electrical conductivity in the memory 15 in association with the information of a date and hour, an eye direction, and a distance from the marine radar.

Then, the salinity estimation unit $11f$ of the control unit 11 uses the value of the electrical conductivity calculated in the processing of S5 to estimate salinity (S6).

Specifically, the salinity estimation unit $11f$ reads from the memory 15 the value of the ratio $K_{15}$ of the electrical conductivity stored in the memory 15 in the processing of S5 and assigns this value to Expression 11 to calculate practical salinity PS.

Moreover, the salinity estimation unit $11f$ stores the calculated value of the practical salinity PS in the data server 16 as a salinity estimation result DB $16d$ in association with the information of a date and hour, an eye direction, and a distance from the marine radar.

Additionally, when the control unit 11 has executed the processing of all pieces of data of the received power in the measurement time zone DB $16c$, it terminates the processing about the measurement time zone DB $16c$ (END).

Here, as described above, in the present invention, an average value of noise values (i.e., a noise floor) $RSIn_m'$ may be used in place of the primary scattering intensity ($RSI_m'$) as the received power in the measurement time zone in which water quality of the seawater is measured. Further, when using the noise floor $RSIn_m'$ of the received power, since the noise floor is not affected by the ocean wave, processing for estimating (S1) the ocean wave spectrum deviation is not executed. In other words, the deviation $\Delta S'$ of the ocean wave spectrum term S is processed as zero. In this case, since the noise floor is an average value excluding peak portions of the received power near 0 Hz and portions near the primary scattering, it can be considered that the salinity in the marine area is lower than the salinity estimated using the noise floor as the received power. Therefore, when the noise floor is used as the received power in the measurement time zone, a maximum value of the salinity in the observation marine area is estimated.

Figure 7:
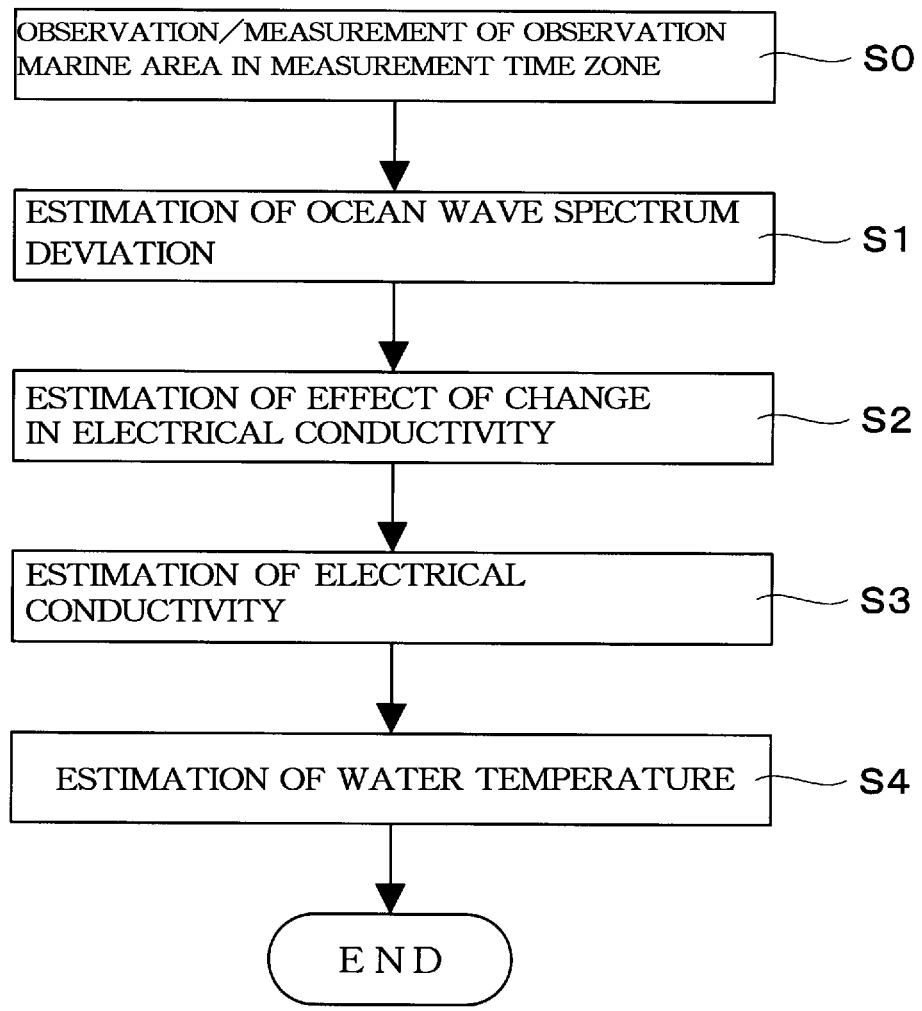
FIG. 7 is a flowchart for explaining a water temperature measuring method for a marine surface layer according to second and third embodiments.
Figure 8:
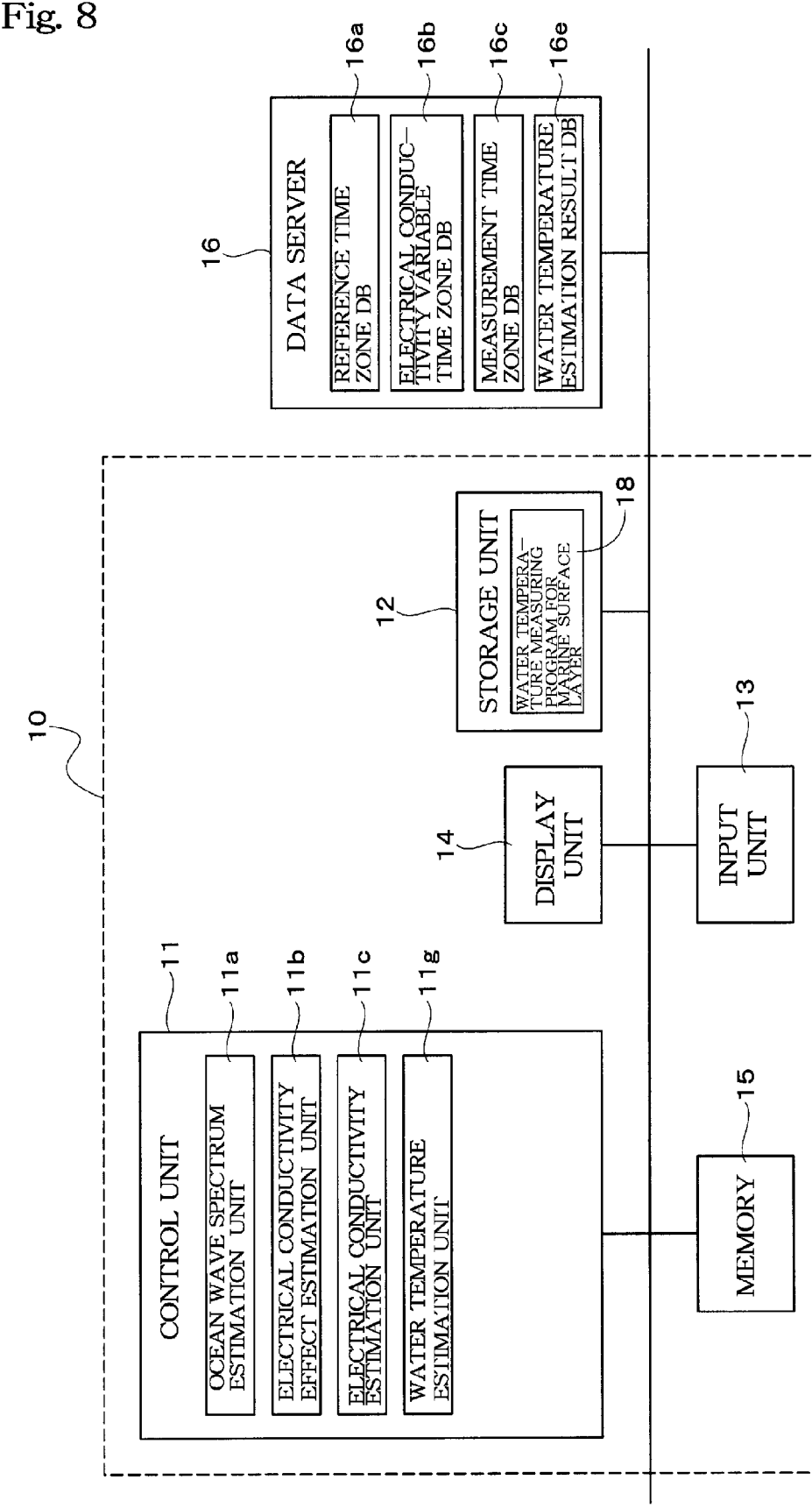
FIG. 8 is a functional block diagram of a water quality measuring device when carrying out the water temperature measuring method for a marine surface layer according to the second and third embodiments by using a program.

Next, FIG. 7 and FIG. 8 show an example of a water quality measuring method, a water quality measuring device, and a water quality measuring program for marine surface layers according to a second embodiment of the present invention when measuring a water temperature in a marine surface layer. As shown in FIG. 7, the water temperature measuring method for marine surface layers according to this embodiment comprises: a step (S1) of estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; a step (S2) of estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies and of estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; a step (S3) of estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and a step (S4) of estimating a value of a water temperature $T_c$ in the measurement time zone by using $\sigma_c=\sigma_0\{1+\alpha(T_c-T_0)\}$ (where $T_0$: a water temperature in the reference time zone, $\alpha$: a temperature correction coefficient).

It is to be noted that the water temperature measuring method according to the second embodiment of the present invention can be applied when salinity of seawater at each point in an observation marine area is fixed and invariable in a reference time zone and a measurement time zone.

The water temperature measuring method for marine surface layers is realized as a water temperature measuring device for marine surface layers. The water temperature measuring device according to this embodiment comprises: means for estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies, and for estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and means for estimating a value of a water temperature $T_c$ in the measurement time zone by using $\sigma_c=\sigma_0\{1+\alpha(T_c-T_0)\}$ (where $T_0$: a water temperature in the reference time zone, $\alpha$: a temperature correction coefficient).

The water temperature measuring device for marine surface layers is also realized by executing a water temperature measuring program for marine surface layers in a computer. In this embodiment, description will be given as to an example where the water temperature measuring program for marine surface layers is executed in a computer.

FIG. 8 shows an overall structure of a water quality measuring device 10 as the water temperature measuring device according to this embodiment configured to execute a water temperature measuring program 18 for marine surface layers. A control unit 11, a storage unit 12, an input unit 13, a display unit 14, and a memory 15 concerning this water quality measuring device 10, and a data server 16 connected to the water quality measuring device 10 are equal to those in the first embodiment, thereby omitting detailed description thereof.

Further, based on execution of the water temperature measuring program 18 for marine surface layers, the control unit 11 of the water quality measuring device 10 is constituted of: an ocean wave spectrum estimation unit 11a as means for estimating a deviation $\Delta S'$ between effect of an ocean wave on received power $RSI_0'$ observed by a marine radar in a reference time zone and effect of an ocean wave on received power $RSI_m'$ in a measurement time zone by using data of the ocean wave or a wind velocity in the reference time zone that electrical conductivity of seawater does not change and data of the ocean wave or a wind velocity in the measurement time zone that water quality of the seawater is measured; an electrical conductivity effect estimation unit 11b as means for estimating a deviation $\Delta s'$ between the effect of the ocean wave on the received power $RSI_0'$ in the reference time zone and effect of an ocean wave on received power in an electrical conductivity variable time zone by using data of the ocean wave or the wind velocity in the reference time zone and data of the ocean wave or a wind velocity in the electrical conductivity variable time zone that the electrical conductivity of the seawater varies and also estimating a regression function $f(\sigma)$ of a relationship between received power obtained by subtracting the deviation $\Delta s'$ from the received power observed by the marine radar in the electrical conductivity variable time zone and the electrical conductivity $\sigma$ in the electrical conductivity variable time zone; an electrical conductivity estimation unit 11c as means for estimating a value of electrical conductivity $\sigma_0$ in a measurement time zone by using $RSI_0'-RSI_m'=\Delta S'+\{f(\sigma_0)-f(\sigma_c)\}$ (where $\sigma_0$: electrical conductivity in the reference time zone); and a water temperature estimation unit 11g as means for estimating a value of a water temperature $T_c$ in a measurement time zone by using $\sigma_c=\sigma_0\{1+\alpha(T_c-T_0)\}$ (where $T_0$: a water temperature in the reference time zone, $\alpha$: a temperature correction coefficient).

Furthermore, in the second embodiment, likewise, a reference time zone DB 16a, an electrical conductivity variable time zone DB 16b, and a measurement time zone DB 16c are prepared.

In regard to the reference time zone DB 16a, a value of a surface layer water temperature in the reference time zone (which is fixed without varying in this time zone) is also prepared as combination data in addition to the same data in the first embodiment.

It is preferable to conduct the measurement of a water temperature in the reference time zone in an eye direction of a marine radar that observes an observation marine area or at a point close to the eye direction, also preferable to carry out this measurement at a plurality of points in the observation marine area, and also desirable to perform this measurement at a point equal to or close to a measurement point for an ocean wave or a wind velocity in the reference time zone, the electrical conductivity variable time zone, or a measurement time zone.

Furthermore, a value of surface layer water temperature in the reference time zone is stored in the reference time zone DB 16a as combination data added to the contents described in the first embodiment in association with information of an eye direction which is the closest to a water temperature measurement point and a distance from the marine radar.

The electrical conductivity variable time zone DB 16b is prepared like the first embodiment.

The measurement time zone DB 16c is prepared like the first embodiment except a water temperature.

Moreover, in this embodiment, processing of S1 to S4 is executed using data in the reference time zone prepared in the reference time zone DB 16a, data in the electrical conductivity variable time zone prepared in the electrical conductivity variable time zone DB 16b, and data in the measurement time zone stored in the measurement time zone DB 16c.

Since processing of S1 to S3 in the second embodiment for measuring a water temperature in a marine surface layer is equal to the processing of S1 to S3 in the first embodiment for measuring salinity in a marine surface layer, description on the processing of S1 to S3 will be omitted and processing of S4 following the processing of S3 will be explained in the second embodiment.

The water temperature estimation unit 11g of the control unit 11 uses a value of electrical conductivity estimated in the processing of S3 to estimate a water temperature (S4). It is to be noted that the processing of S4 is carried out for each data of received power recorded in the measurement time zone DB 16c in accordance with each date and hour in the measurement time zone (in other words, the processing is carried out in accordance with each eye direction of the marine radar and each distance from the marine radar).

Specifically, the water temperature estimation unit 11g reads from the memory 15 a value of electrical conductivity $\sigma_c$ in the measurement time zone stored in the memory 15 in the processing of S3, reads from the reference time zone DB 16a a value of electrical conductivity $\sigma_0$ and a value of a water temperature $T_0$ in the reference time zone, and assigns these values to Expression 25 to estimate a surface layer water temperature $T_c$ in the measurement time zone. It is to be noted that Expression 25 is derived from Expression 12. Expression 25, including a value of a temperature correction coefficient $\alpha$, is defined in the water temperature measuring program 17 for marine surface layers.

$$\sigma(T_c)=\sigma(T_0)\{1+\alpha(T_c-T_0)\} \qquad \text{(Expression 25)}$$

where T: a water temperature;

σ: electrical conductivity; and

α: a temperature correction coefficient (approximately 0.01 to 0.03).

Furthermore, a subscript 0 represents electrical conductivity or a water temperature in the reference time zone; and a subscript c represents electrical conductivity or a water temperature in the measurement time zone.

It is to be noted that $\sigma(T_c)=\sigma_0$ and $\sigma(T_0)=\sigma_0$ are achieved.

It is to be noted that a value of the electrical conductivity $\sigma_0$ and a value of the water temperature $T_0$ associated with an eye direction and a distance which are the closest to an eye direction and a distance associated with a value of the electrical conductivity $\sigma_0$ read from the memory 15 are selected from values of the electrical conductivity $\sigma_0$ and values of the water temperature $T_0$ stored in the reference time zone DB 16a, and the selected value is used.

Moreover, the water temperature estimation unit 11g stores the estimated value of the water temperature $T_c$ in the data server 16 as the water temperature estimation result DB 16e in association with information of a date and hour, an eye direction, and a distance from the marine radar.

Additionally, when the control unit 11 has executed the processing of all pieces of data of the received power in the measurement time zone DB 16c, it terminates the processing about the measurement time zone DB 16c (END).

Description will now be given as to an example of a water quality measuring method, a water quality measuring device, and a water quality measuring program for marine surface layers according to the present invention when measuring a water temperature in a marine surface layer by a method different from the second embodiment as a third embodiment of the present invention. It is to be noted that a flowchart for explaining the water temperature measuring method for marine surface layers according to the third embodiment is equal to that in FIG. 7 used for explaining the second embodiment.

The water temperature measuring method for marine surface layers according to this embodiment comprises: a step (S1) of estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; a step (S2) of estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies, and of estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; a step (S3) of estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and a step (S4) of estimating a value of a water temperature $T_c$ in the measurement time zone by using $K_{15}=\sigma_c/[\sigma_{KCl}(15)\{1+\alpha(T_c-15)\}]$ and $PS=0.008-0.1692K_{15}^{0.5}+25.3851K_{15}+14.0941K_{15}^{1.5}-7.0261K_{15}^{2}+2.708\,1K_{15}^{2.5}$ (where $\sigma_{KCl}(15)$: electrical conductivity of a standard solution of a potassium chloride in a standard state of 15° C. and 1 atmosphere, α: a temperature correction coefficient, PS: salinity in the measurement time zone).

It is to be noted that the water temperature measuring method according to the third embodiment of the present invention can be applied when salinity of seawater at each point in an observation marine area in the measurement time zone is known. Therefore, when the salinity of the seawater varies in the observation marine area, the second embodiment cannot be used for the measurement of a water temperature, but the third embodiment can be used. On the other hand, when the salinity of the seawater does not vary in the observation marine area in the reference time zone and the measurement time zone, either the second embodiment or the third embodiment can be used.

The water temperature measuring method for marine surface layers is realized as a water temperature measuring device for marine surface layers. The water temperature measuring device according to this embodiment comprises: means for estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies, and for estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and means for estimating a value of a water temperature $T_c$ in the measurement time zone by using $K_{15}=\sigma_c/[\sigma_{KCl}(15)\{1+\alpha(T_c-15)\}]$ and $PS=0.008-0.1692K_{15}^{0.5}+25.3851K_{15}+14.0941K_{15}^{1.5}-7.0261K_{15}^2+2.708\ 1K_{15}^{2.5}$ (where $\sigma_{KCl}(15)$: electrical conductivity of a standard solution of a potassium chloride in a standard state of 15° C. and 1 atmosphere, $\alpha$: a temperature correction coefficient, PS: salinity in the measurement time zone).

The water temperature measuring device for marine surface layers can be also realized by executing a water temperature measuring program for marine surface layers in a computer. In this embodiment, description will be given as to an example that the water temperature measuring program for marine surface layers is executed in a computer. It is to be noted that an overall configuration of a water quality measuring device as a water temperature measuring device configured to execute the water temperature measuring program for marine surface layers according to the third embodiment is equal to that shown in FIG. 8 used in the explanation of the second embodiment, and a control unit 11, a storage unit 12, an input unit 13, a display unit 14, and a memory 15 concerning the water quality measuring device and a data server 16 connected to the water quality measuring device are equal to those in the first and second embodiments, thereby omitting detailed description thereof.

Moreover, based on execution of the water temperature measuring program for marine surface layers according to the third embodiment, the control unit 11 of a water quality measuring device 10 is constituted of: an ocean wave spectrum estimation unit 11a as means for estimating a deviation $\Delta S'$ between effect of an ocean wave on received power $RSI_0'$ observed by a marine radar in a reference time zone and effect of an ocean wave on received power $RSI_m'$ in a measurement time zone by using data of the ocean wave or a wind velocity in the reference time zone that electrical conductivity of seawater does not change and data of the ocean wave or a wind velocity in the measurement time zone that water quality of the seawater is measured; an electrical conductivity effect estimation unit 11b as means for estimating a deviation $\Delta s'$ between the effect of the ocean wave on the received power $RSI_0'$ in the reference time zone and effect of an ocean wave on received power in an electrical conductivity variable time zone by using data of the ocean wave or the wind velocity in the reference time zone and data of the ocean wave or a wind velocity in the electrical conductivity variable time zone that the electrical conductivity of the seawater varies and also estimating a regression function $f(\sigma)$ of a relationship between received power obtained by subtracting the deviation $\Delta s'$ from the received power observed by the marine radar in the electrical conductivity variable time zone and the electrical conductivity $\sigma$ in the electrical conductivity variable time zone; an electrical conductivity estimation unit 11c as means for estimating a value of electrical conductivity $\sigma_c$ in a measurement time zone by using $RSI_0'-RSI_m'=\Delta S'+\{f(\sigma_0)-f(\sigma_c)\}$ (where $\sigma_0$: electrical conductivity in the reference time zone); and a water temperature estimation unit 11g as means for estimating a value of a water temperature $T_c$ in a measurement time zone by using $K_{15}=\sigma_c/[\sigma_{KCl}(15)\{1+\alpha(T_c-15)\}]$ and $PS=0.008-0.1692K_{15}^{0.5}+25.3851K_{15}+14.0941K_{15}^{1.5}-7.0261K_{15}^2+2.708\ 1K_{15}^{2.5}$ (where $\sigma_{KCl}(15)$: electrical conductivity of a standard solution of a potassium chloride in a standard state of 15° C. and 1 atmosphere, $\alpha$: a temperature correction coefficient, PS: salinity in the measurement time zone).

Additionally, in the third embodiment, likewise, a standard time zone DB 16a, an electrical conductivity variable time zone DB 16b, and a measurement time zone DB 16c are prepared.

The reference time zone DB 16a and the electrical conductivity variable time zone DB 16b are prepared like the first embodiment.

In regard to the measurement time zone DB 16c, a value of salinity of the seawater is prepared as combination data in place of a water temperature in the first embodiment.

It is preferable to conduct the measurement of salinity in the measurement time zone in an eye direction of a marine radar that observes an observation marine area or at a point close to the eye direction, also preferable to carry out this measurement at a plurality of points in the observation marine area, and also desirable to perform this measurement at a point equal to or close to a measurement point for an ocean wave or a wind velocity in the reference time zone, the electrical conductivity variable time zone, or the measurement time zone.

Moreover, in this embodiment, processing of S1 to S4 is executed using data in the reference time zone prepared in the reference time zone DB 16a, data in the electrical conductivity variable time zone prepared in the electrical conductivity variable time zone DB 16b, and data in the measurement time zone stored in the measurement time zone DB 16c.

Since processing of S1 to S3 in the third embodiment for measuring a water temperature in a marine surface layer is equal to the processing of S1 to S3 in the first embodiment for measuring salinity in a marine surface layer, description on the processing of S1 to S3 will be omitted and processing of S4 following the processing of S3 will be explained in the third embodiment.

The water temperature estimation unit 11g of the control unit 11 uses a value of electrical conductivity estimated in the processing of S3 to estimate a water temperature (S4). It is to be noted that the processing of S4 is carried out for each data of received power recorded in the measurement time zone DB 16*c* in accordance with each date and hour in the measurement time zone (in other words, the processing is carried out in accordance with each eye direction of the marine radar and each distance from the marine radar).

Specifically, the water temperature estimation unit 11*g* reads from the memory 15 a value of electrical conductivity $\sigma_c$ in the measurement time zone stored in the memory 15 in the processing of S3, and reads from the measurement time zone DB 16*c* a value of salinity PS of the seawater in the measurement time zone.

Further, the water temperature estimation unit 11*g* uses the value of the electrical conductivity $\sigma_c$, the value of the salinity PS, Expression 26, and Expression 11 to estimate a surface layer water temperature $T_c$ in the measurement time zone. It is to be noted that Expression 26 is derived from Expression 24 and Expression 12. Expression 26 is defined in the water temperature measuring program 17 for marine surface layers together with a value of the temperature correction coefficient $\alpha$ and a value of the electrical conductivity $\sigma_{KCl}(15)$ of a standard solution of the potassium chloride in the standard state of 15° C. and 1 atmosphere.

$$K_{15} = \sigma(T_c)/[\sigma_{KCl}(15)\{1+\alpha(T_c-15)\}] \qquad \text{(Expression 26)}$$

where $K_{15}$: a ratio of the electrical conductivity of the seawater to the electrical conductivity $\sigma_{KCl}(15)$ of the standard solution of the potassium chloride in the standard state of 15° C. and 1 atmosphere;

$\sigma(T_c)$: electrical conductivity in the measurement time zone;

$T_c$: a water temperature in the measurement time zone; and $\alpha$: a temperature correction coefficient (approximately 0.01 to 0.03).

It is to be noted that $\sigma(T_c) = \sigma_0$ is achieved.

It is to be noted that a value of the salinity PS associated with an eye direction and a distance which are the closest to an eye direction and a distance associated with a value of the electrical conductivity $\sigma_c$ read from the memory 15 are selected from values of the salinity PS stored in the measurement time zone DB 16*c*, and the selected value is used.

Moreover, the water temperature estimation unit 11*g* stores the estimated value of the water temperature $T_c$ in the data server 16 as the water temperature estimation result DB 16*e* in association with information of a date and hour, an eye direction, and a distance from the marine radar.

Additionally, when the control unit 11 has executed the processing of all pieces of data of the received power in the measurement time zone DB 16*c*, it terminates the processing about the measurement time zone DB 16*c* (END).

According to the water quality measuring method, the water quality measuring device, and the water quality measuring program for marine surface layers of the present invention having the above-described configuration, since the received power observed by the marine radar can be used to calculate the electrical conductivity and this electrical conductivity can be used to estimate the salinity or the water temperature of the seawater in the observation marine area, a radar obtained by the marine radar can be effectively exploited, and a time or a cost required for the measurement of the salinity or the water temperature of the seawater covering a marine area in the range of several tens of km can be reduced.

It is to be noted that the foregoing embodiments are preferred embodiments of the present invention, but the present invention is not restricted thereto, and it can be modified in many ways without departing from the scope of the present invention. For example, although the processing using the practical salinity as a premise has been described in the foregoing embodiments, the present invention is not restricted thereto, and absolute salinity [‰] may be used.

Furthermore, although the various DBs 16*a* to 16*e* are stored in the data server 16 in the foregoing embodiments, but the present invention is not restricted thereto, and these DBs may be stored in the storage unit 12.

EXAMPLE 1

To verify validity of a salinity arithmetic result obtained by the salinity measuring method for marine surface layers according to the present invention, the salinity arithmetic result using the present invention was compared with an actual measurement result. Description will be given in association with processing steps in a flowchart of FIG. 1. It is to be noted that electrical conductivity $EC_k = 4.0$ Sm$^{-1}$ and a temperature correction coefficient $\alpha = 0.02$ are set in this embodiment.

(1) Observation/Measurement in Observation Marine Area (S0)

Figure 9:
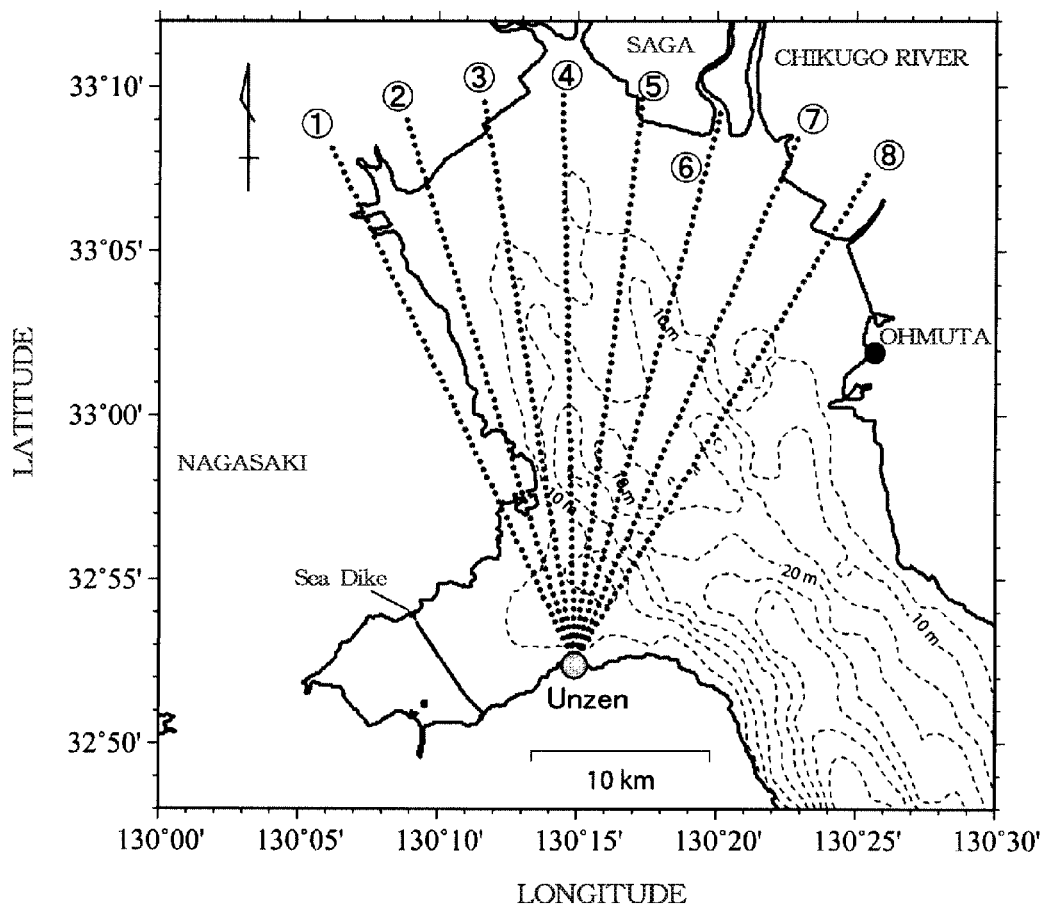
FIG. 9 is a view for explaining an installation position and observing directions of the marine radar according to Example 1.

As observation data of a marine radar, this embodiment adopted a result of observation carried out in 2006 to 2008 at the mouth of Isahaya bay using a marine radar installed in Unzen city, Nagasaki Prefecture (a position of a circle mark immediately above the indication UNZEN in FIG. 9).

In the observation, a marine radar in a VHF band (an electric wave frequency: 41.9 MHz) developed by Central Research Institute of Electric Power Industry (Shinichi Sakai, et al.: High-performance Coastal Marine Radar for Wide Area Flow Observation, Research Report of Central Research Institute of Electric Power Industry, U02056, 2003) was used.

In this embodiment, a marine radar constituted of one transmitting antenna and eight receiving antennas was used. One observation time was 12 minutes per station, and transmission/reception of electric waves was performed for four times. To avoid cross talk of the electric waves at both observation points, the observation points were switched to perform observation every 15 minutes at an interval of 3 minutes. A Frequency Modulated Interrupted Continuous Wave system (which is also called an FMICW system) was used as a transmission/reception method, and a sweep frequency width was 300 kHz. A received electric wave was resolved into eight directions using a Digital Beam. Forming (which is also called DBF). The resolved observation directions will be referred to as eye directions or beam directions, and numbers from 1 to 8 are set in a clockwise direction as shown in FIG. 9.

A technique of Tsubono and others characterized in that primary scattering is less miscalculated was used for detection of the primary scattering in a Doppler spectrum (see Japanese Unexamined Patent Application Publication No. 2009-75017). Further, data that the primary scattering cannot be calculated using this technique was treated as missing observation.

A wind gauge, a rain gauge, a thermometer, and a hygrometer were installed in each observing station, and observation was carried out every 10 minutes.

(2) Estimation of Deviation of Effect of Wind Velocity (S1)—Examination of Ocean Wave Spectrum Term Observation data of received power corresponding to a total of 5586 times from Dec. 22 in 2006 to Apr. 18 in 2007 (which will be referred to as a target period hereinafter) was used for examination of an ocean wave spectrum term. Since an amount of rainfall around an observation marine area was small in the target period, there was speculation that a reduction in salinity in the marine area due to river water hardly occurred, and hence it was considered that electrical conductivity hardly changed due to a fluctuation in salinity. Furthermore, a water temperature in the observation marine area fluctuated approximately 7° C. during the target period. A change in electrical conductivity involved by this fluctuation of water temperature might possibly affect the received power. Therefore, it was considered that the fluctuation of water temperature appears as a variation in received power.

The ocean wave spectrum term was examined using received power data of <Beam 8, a point of 3 km> of Unzen station that enabled sufficient acquisition of the received power during the target period and that was close to an observing station of a wind velocity.

Figure 10:
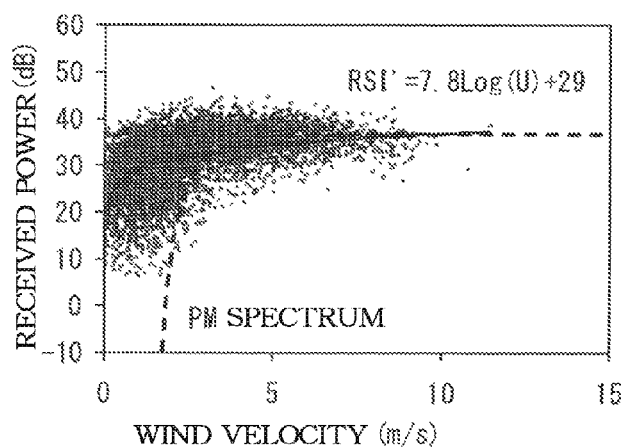
FIG. 10 is a plotted diagram of data that is a combination of a wind velocity and received power according to Example 1.

The received power of <Beam 8, the point of 3 km> in the target period and a wind velocity measured in Unzen station at the same time were sorted as combination data, thereby obtaining a result depicted in FIG. 10 (in the drawing, dark circles represent plotting of the combination data). Here, a solid line in FIG. 10 indicates an approximate expression (Expression 21, Expression 27) when a logarithmic function is applied to an actual measurement value (i.e., the combination data of the wind velocity and the received power). Further, a broken line in FIG. 10 indicates received power based on a PM spectrum (Expression 20). It is to be noted that an intercept $B_2$ ($L_R$) in Expression 20 was adjusted in such a manner that received power when a wind velocity is 10 ms$^{-1}$ coincides with a value obtained from the approximate expression.

It was observed from FIG. 10 that the actually measured received power greatly fluctuates but the received power tends to be entirely lowered when the wind velocity is lower than approximately 3 ms$^{-1}$. It was considered that this tendency is caused by a reduction in ocean wave spectrum.

In FIG. 10, the PM spectrum greatly deviated from an actual measurement value when the wind velocity is lower than 4 ms$^{-1}$. As a result, in this example, it was determined that estimating the ocean wave spectrum term using the PM spectrum is difficult. Therefore, an approximate curve obtained by applying the logarithmic function to the actual measurement value was used as a calculation formula for the ocean wave spectrum term. Specifically, the combination data of the wind velocity and the received power depicted in FIG. 10 was used to estimate a regression coefficient $a_1$ and a constant term $b_1$ of Expression 21, thereby using a resultant approximate curve. It is to be noted that the observation marine area is an inner bay and ocean waves are hardly propagated from the outer sea, and hence it can be considered that ocean waves are not produced when the wind velocity is 0 ms$^{-1}$. Furthermore, to reproduce a relationship that the received power becomes negative infinite when an observation target wave is not present, approximation using the logarithmic function was carried out. Moreover, a least-square method was used for the approximation. A resultant approximate expression is as represented by Expression 27.

$$RSI'=7.8 \, \text{Log}(U)+29 \tag{Expression 27}$$

It was confirmed from FIG. 10 that a rough tendency of the actual measurement value is held by the approximate curve (a broken line in the drawing). A value of an intercept 29 in Expression 27 corresponds to a sum of $B_1$, X', and A' in Expression 7, and it is a value that is not affected by the wind velocity. In Expression 10, a value of the intercept is offset to use a difference in received power at each observing position. As a result, in this embodiment, Expression 28 was used as the ocean wave spectrum term in Expression 10.

$$\Delta S'=7.8(\text{Log}(U_1)-\text{Log}(U_0)) \tag{Expression 28}$$

(3) Estimation of Effect of Change in Electrical Conductivity (S2)—Examination of Electrical Conductivity Term Subsequently, an effect term $Z(\sigma)$ of the electrical conductivity in Expression 10 was obtained. However, an effect term $X'(\sigma)$ of the electrical conductivity included in $Z(\sigma)$ on a scattering cross section is unclear, and hence $Z(\sigma)$ including an effect $A_1'(\sigma)$ of propagation loss was empirically calculated from an observation result.

Specifically, combination data of received power and salinity at a point that is 1 m below a water surface from July 2 to 14 in 2007 including overflow of Chikugo River was used (Takumi Yoshii et al, Effect of Surface Layer Salinity in Marine Radar Observation, Research Report of Central Research Institute of Electric Power Industry, V09003, 2009). This combination data was used, and a result shown in FIG. 11 was obtained as a relationship between electrical conductivity and received power. The received power in the drawing is a value of <Beam 8, a point of 3 km) which is the closest to an observation point of salinity. In regard to an ocean wave spectrum term, a wind velocity at Unzen station was used to carry out correction based on Expression 28, thereby correcting the received power into received power when the wind velocity is sufficiently obtained.

Figure 11:
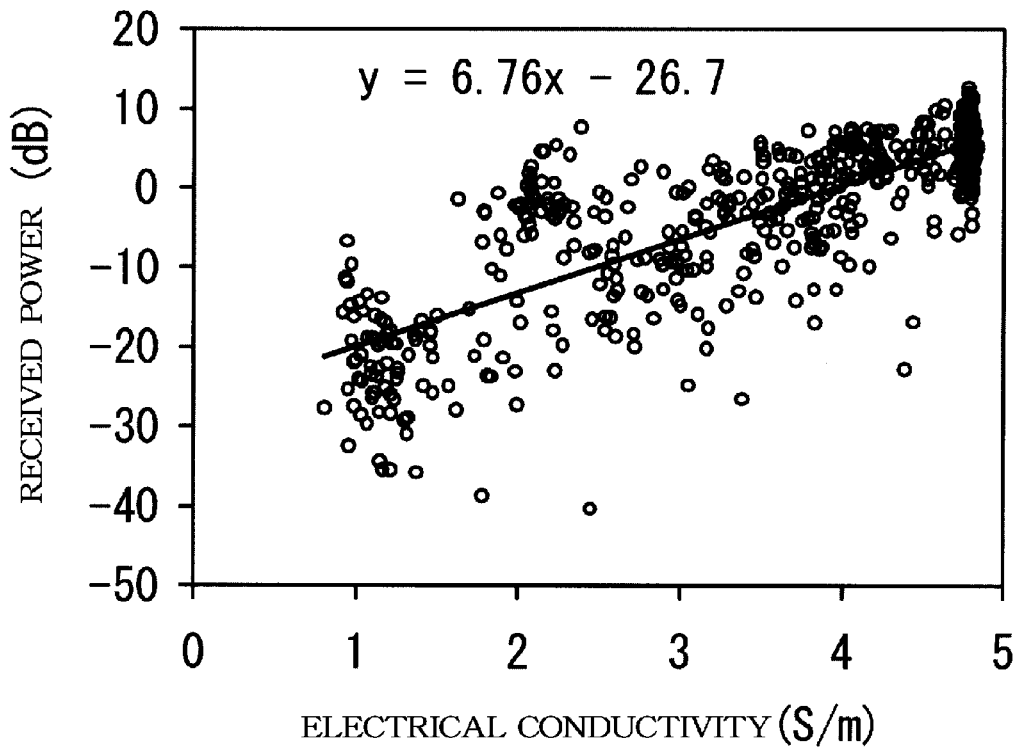
FIG. 11 is a plotted diagram of data that is a combination of electrical conductivity and received power according to Example 1.

In FIG. 11, a linear approximate straight line was applied to a relationship between electrical conductivity σ and received power RSI' by using the least-square method to obtain Expression 29.

$$RSI'(\sigma)=6.76\sigma-26.7 \tag{Expression 29}$$

The approximate straight line represented in Expression 29 is indicated by a dotted line in FIG. 11. A correlation coefficient of the approximate straight line is 0.8, and a standard deviation is 6.38, and it was confirmed from this result that the approximate straight line grasps a tendency of an actually measured value. Here, a first term in a right side of Expression 29 corresponds to $Z(\sigma)$, and a second term in the right side represents a sum of $B_1'$ and S'.

As a result, Expression 29 was assigned to Expression 10 to be organized, and Expression 30 was thereby obtained as an expression that acquires a difference ΔRSI' of the received power using a deviation ΔS' of the ocean wave spectrum and a deviation Δσ of the electrical conductivity.

$$\Delta RSI'(\sigma)=\Delta S'+6.76\Delta\sigma \tag{Expression 30}$$

(4) Estimation of Electrical Conductivity (S3)
(4-1) Outline of Observation

Figure 12:
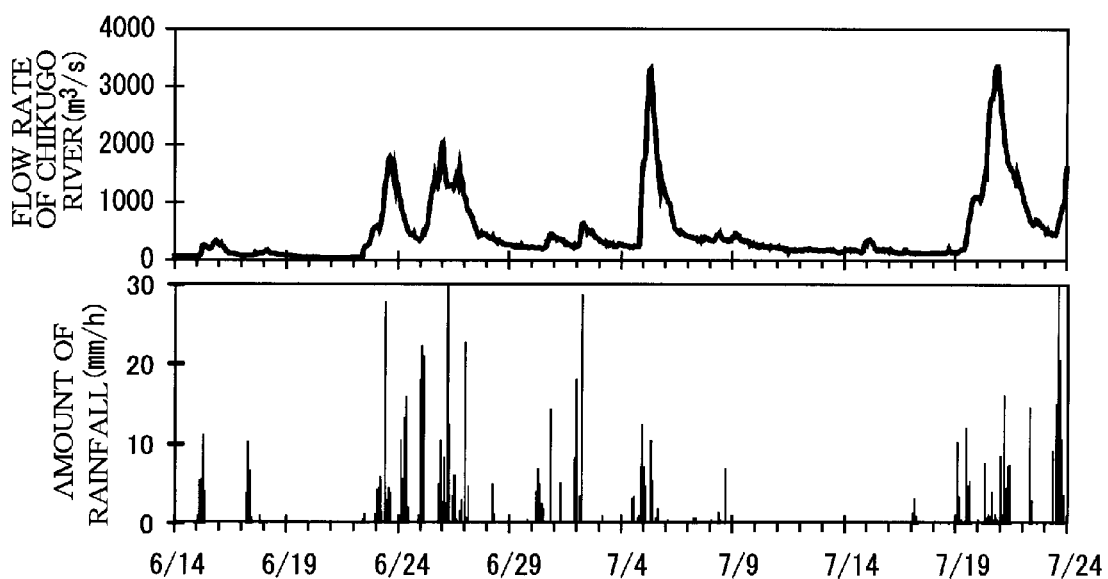
FIG. 12 is a view showing fluctuations of a flow volume of Chikugo River and rainfall according to Example 1.

First, FIG. 12 shows fluctuations in a flow volume of Chikugo River and an amount of rainfall in June 14 to July 24 in 2006 (which will be referred to as an observation period hereinafter). It was revealed from FIG. 12 that a large-scale overflow occurred from Chikugo River three times around June 24, in July 5, and a period from July 19 to 22 during the summer season in 2006. It is to be noted that installing positions and eye directions of the marine radar that collected received power data during the observation period were equal to those in FIG. 9.

Further, according to an existing observation result of salinity in a closed-off section of Ariake Sea bay, it was found out that an inner section of the bay had been already stratified at a time point of June 26 in 2006 and the salinity in a surface layer was lowered to approximately 15. Furthermore, it was revealed that the salinity in the surface layer was reduced due to the overflow in July 6 and July 20. In particular, it was understood that a range of reduction in salinity in July 20 was large and the salinity in the surface layer was reduced to approximately 5 (Takaharu Hamada, et al.: Flow in Closed-off Section of Ariake Sea and Conveyance of Suspended Matters—Consideration based on On-site Observation and Numeric Mode—, Collected Accomplishment Reports of Ariake Sea Research Project in Saga University, Vol. 3, pp. 87-92, 2007; Takaharu Hamada, et al.: Observation of Forming/dissolving Process of Dysoxic Water Mass in Closed-off Section of Ariake Sea, Vol. 54, pp. 1121-1125, 2007; Kenji Yoshino, et al.: Effect of Dysoxic Water Mass on Benthic Assemblages in Closed-off Section of Ariake Sea Bay, Collected Accomplishment Reports of Ariake Sea Research Project in Saga University, Vol. 4, pp. 15-21, 2008).

Moreover, it was understood from a result of observation in the observation marine area that a fluctuation in water temperature in the surface layer during the observation period is approximately 3° C. and the fluctuation is small. Additionally, since a water temperature in the surface layer is substantially equal to those in middle and bottom layers, it was inferred that temperature stratification was not formed. Based on this fact, it was considered that a fluctuation in electrical conductivity during the observation period is mainly caused due to a fluctuation in surface layer salinity.

(4-2) Calculation of Reference Power

Subsequently, a period from June 18 to 22 having a small river flow rate and no rainfall (observation data corresponding to 193 times) was determined as a reference time, and reference power was obtained. According to a result of observation in the observation marine area, the surface layer salinity in each of the closed-off section of Ariake Sea and the mouth section of Isahaya bay was approximately 32 in June 13. Based on this fact, it was considered that salinity stratification was not formed in the bay at a time point of June 13. Referring to FIG. 12, since a large amount of rainfall or overflow did not occur during the period from June 13 to 22, it was inferred that the salinity stratification was not formed until June 22. Based on these observation results, it was assumed that an average value in the reference time is a value of a site having the uniform surface layer salinity of 32.

Moreover, it was considered from a wind velocity in the reference time that the calculated reference power represents received power with a wind velocity of approximately 2 ms$^{-1}$.

(4-3) Setting of Initial Value

To estimate the surface layer salinity, a water temperature must be known. In this embodiment, a surface layer water temperature during the observation period was assumed to be fixed. That is, it was considered that fluctuations in received power are all caused due to fluctuations in electrical conductivity involved by a change in salinity, and the surface layer salinity was estimated. It was confirmed from the result of observation in the observation marine area that a fluctuation in water temperature in the period shown in FIG. 12 (i.e., the observation period) is 2° C. at a maximum and a fluctuation in salinity is approximately 17. It was considered from FIG. 5 that, since the effect of the surface layer salinity on the electrical conductivity is sufficiently greater than that of the water temperature, the salinity is dominant with respect to a fluctuation in electrical conductivity during the observation period and a fluctuation in water temperature can be ignored. Moreover, the effect of the ocean wave spectrum term was not taken into consideration either. Incidentally, in regard to wind velocities in Unzen Station and Arao Station during the observation period, it was confirmed that wind velocities of approximately 2 ms$^{-1}$ or above occupied the majority, and it was thereby considered that an extreme reduction in ocean wave spectrum was small.

Based on a result of observation in the observation marine area, a surface layer water temperature in the reference time was set to 23° C. Additionally, electrical conductivity in the reference time was set to 4.6 Sm$^{-1}$ based on the fact that salinity is approximately 32 and the water temperature is approximately 23° C. and also based on an observation result of CTD in 2007 (Takumi Yoshii, et al.: Effect of Surface Layer Salinity in Marine Radar Observation, Research Report of Central Research Institute of Electric Power Industry, V09003, 2009).

When these values were used to estimate the salinity in the reference time, approximately 33.6 was obtained, and it was confirmed that this value substantially corresponds to approximately 32 which is a measurement value. Based on this fact, these set values were determined to be appropriate values.

Figure 13:
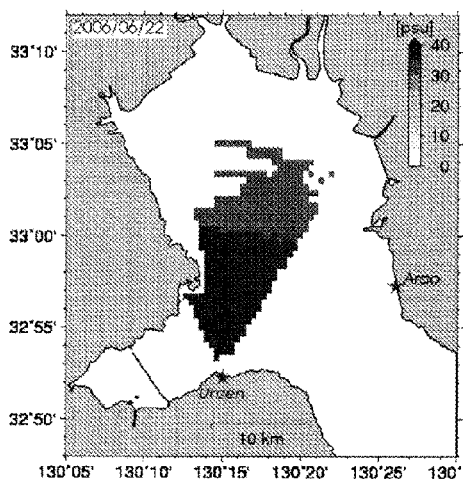
FIG. 13 is a view showing average daily results of estimation of surface layer salinity according to Example 1.
Figure 13:
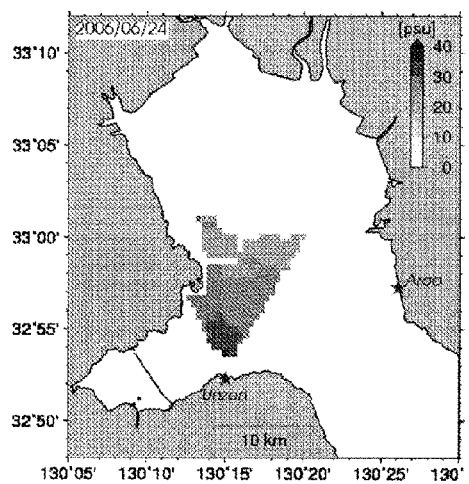
Figure 13:
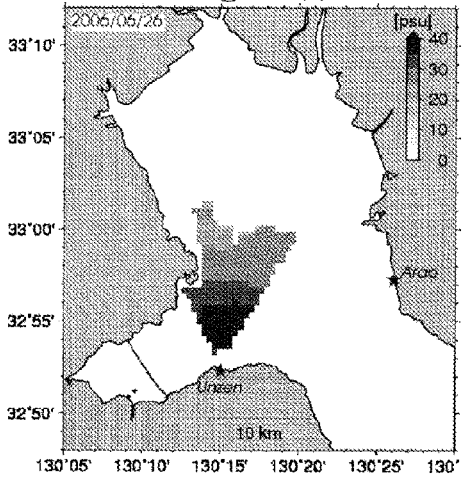
Figure 13:
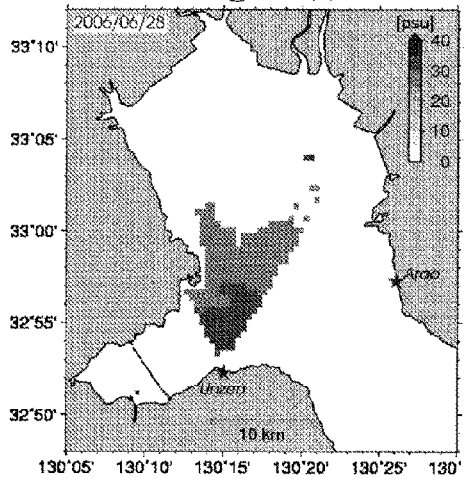
Figure 13:
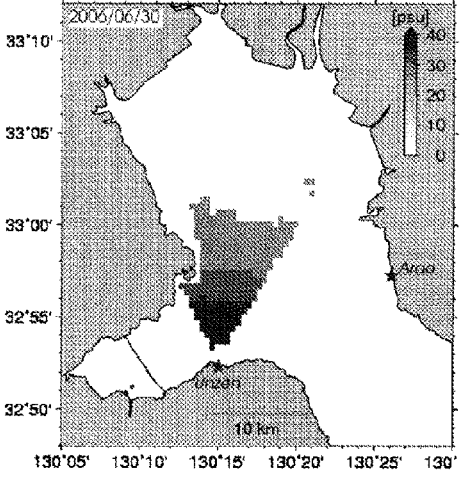
Figure 13:
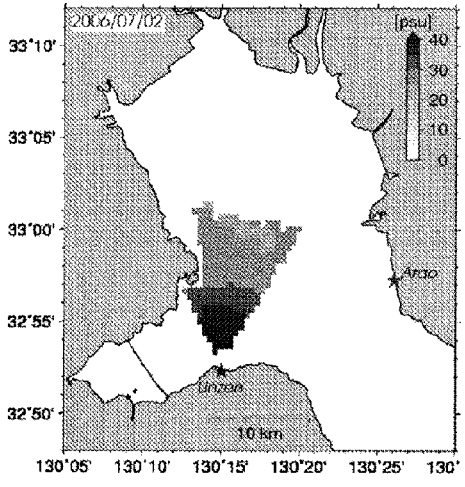
Figure 14:
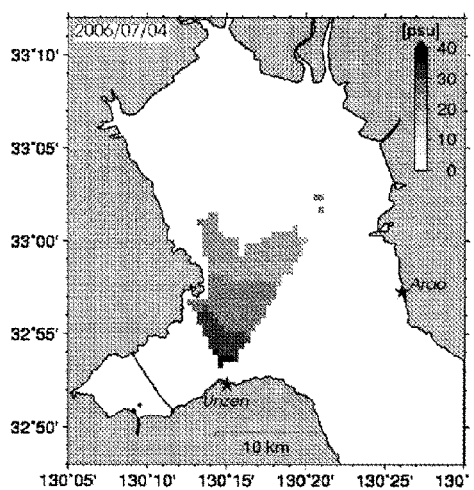
FIG. 14 is a view showing average daily results of estimation of the surface layer salinity according to Example 1.
Figure 14:
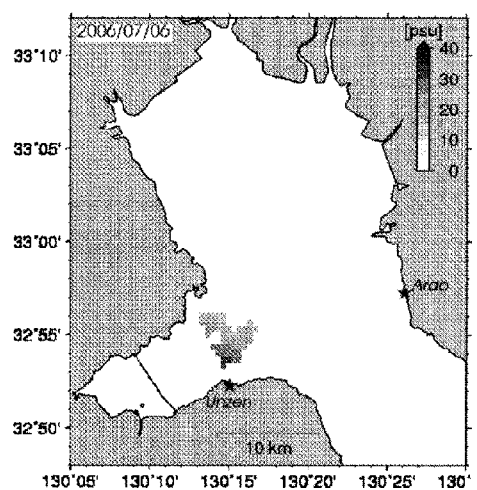
Figure 14:
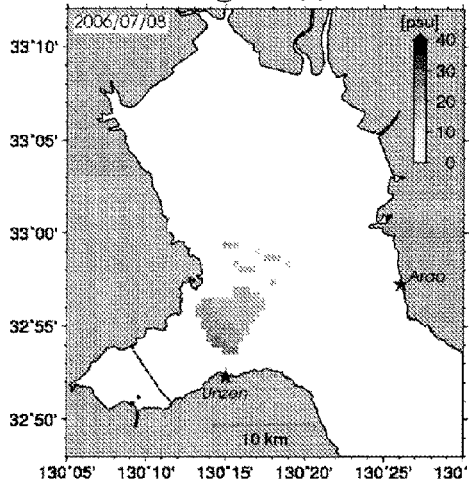
Figure 14:
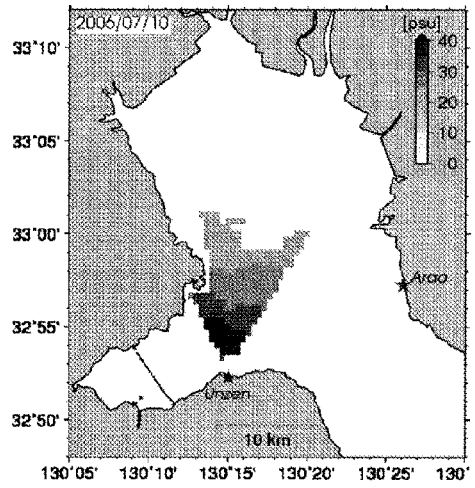
Figure 14:
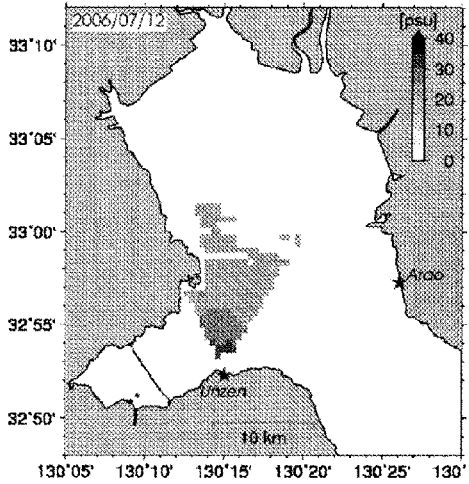
Figure 14:
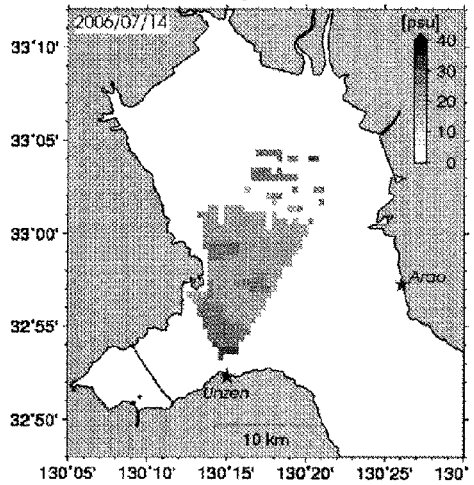

(5) Estimation of Surface Layer Salinity (S6)—When Primary Scattering Intensity is Used In regard to a period from June 22 to July 14 in 2006, primary scattering intensity of received power was used to estimate surface layer salinity and calculate a daily mean, whereby results shown in FIG. 13 and FIG. 14 were obtained.

It was confirmed from FIG. 12 that Chikugo River overflowed from June 23 to 27 and from July 5 to 10 during the observation period and a flow volume during any other period was a flow volume of a long-run average water flow. Further, as described above, since it was confirmed from the observation result that the salinity was high in the entire marine area of Ariake Sea at a time point of June 22, no formation of salinity stratification was supposed.

Furthermore, it was confirmed that an estimation result according to the present invention indicates that the salinity in the observation marine area is high at the time point of June 22 (see FIG. 13(*a*)). It was also confirmed that the estimation result according to the present invention also indicates the surface layer salinity is lowered at the time of the overflow from June 23 to 27 (see FIGS. 13(*b*), (*c*), and (*d*)).

Moreover, it was also confirmed that the estimation result according to the present invention indicates that the surface layer salinity did not recover to the state in June 22 after the long-run average water flow and the low surface layer salinity state was continued in the entire bay (see FIGS. 13(*e*) and (*f*)). This state was determined to correctly reproduce that the salinity stratification was formed in the marine area due to the overflow of Chikugo River from June 23 and the salinity in the surface layer was reduced.

Additionally, the same tendency was also confirmed in the overflow from July 5 to 10 (see FIGS. 14(*a*) to (*f*)). Further, it was also confirmed that the result indicates that the surface layer salinity slightly recovered after July 10 at which a river flow rate was reduced to a value close to a flow rate of the long-run average water flow but the surface layer salinity in the bay was decreased as compared to that in the period from June 28 to July 4. It was considered that this reduction occurred since the salinity stratification was intensified due to the overflow and the surface layer salinity was further reduced.

Furthermore, it was also confirmed from the estimation result of the surface layer salinity that the surface layer salinity is reduced toward the closed-off section of the Ariake Sea (the north side where the river mouth of Chikugo River is present) and the reduction in salinity is propagated toward the south side with the overflow. A main cause of the reduction in salinity in the marine area is considered to be the overflow of the Chikugo River, and hence it is determined that this reduction correctly reproduces that the surface layer salinity is gradually decreased from the north side.

As a result, the surface layer salinity estimated using the observation result of the marine radar at least qualitatively grips the process of forming and developing the salinity stratification in the marine area.

(6) Estimation of Surface Layer Salinity (S6)—When Noise Floor is Used

Figure 15:
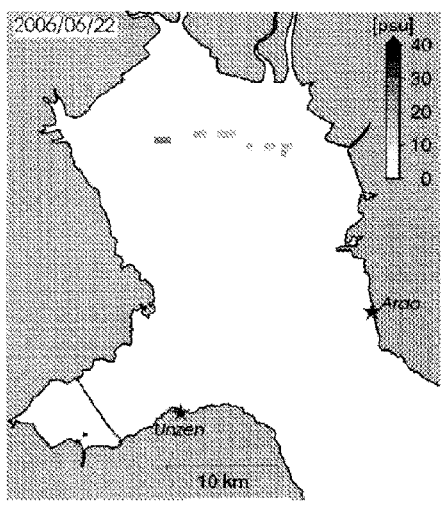
FIG. 15 is a view showing average daily results of estimation of maximum surface layer salinity according to Example 1.
Figure 15:
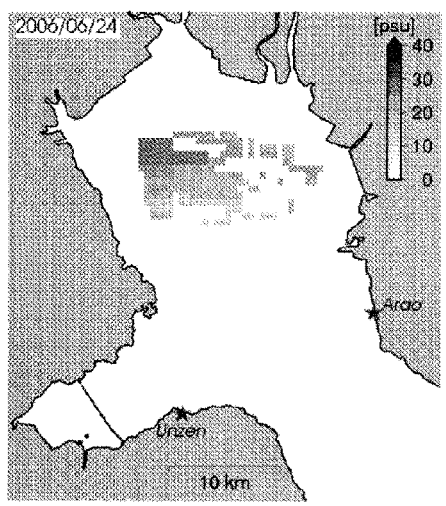
Figure 15:
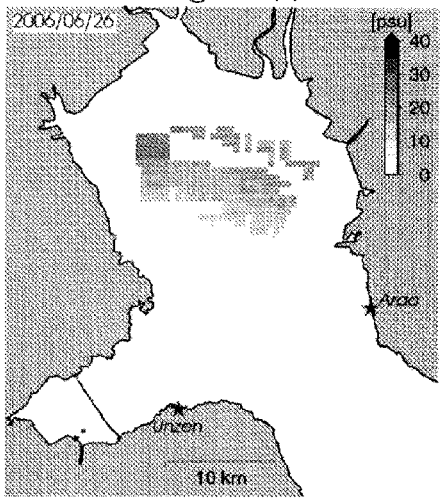
Figure 15:
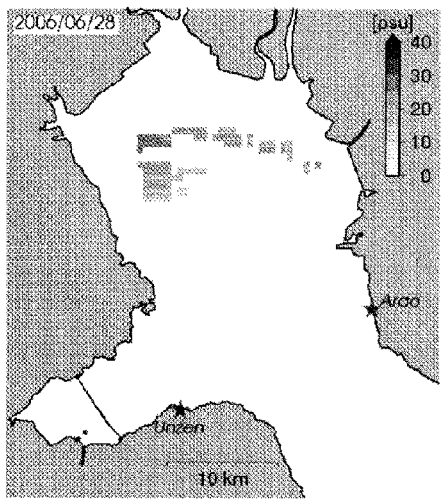
Figure 16:
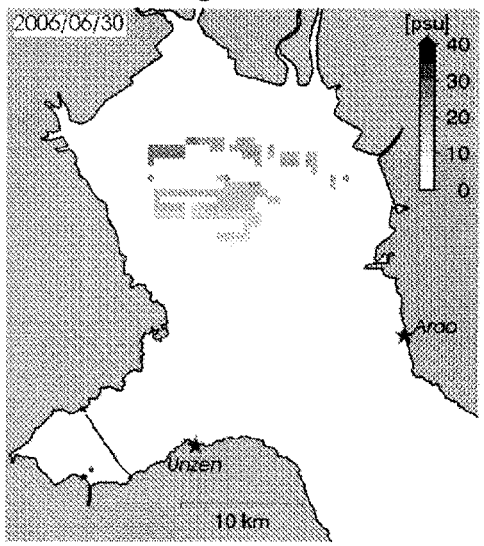
FIG. 16 is a view showing average daily results of estimation of the maximum surface layer salinity according to Example 1.
Figure 16:
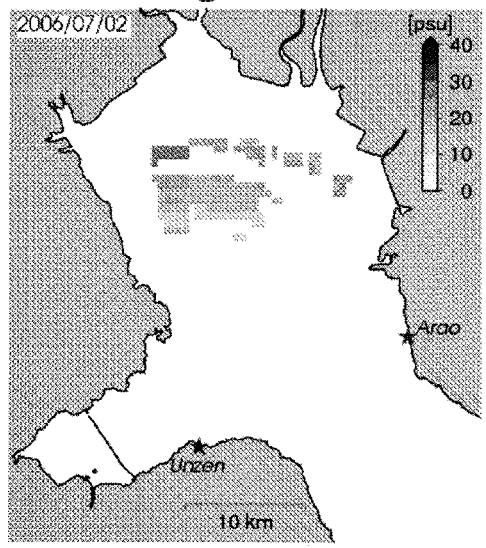
Figure 16:
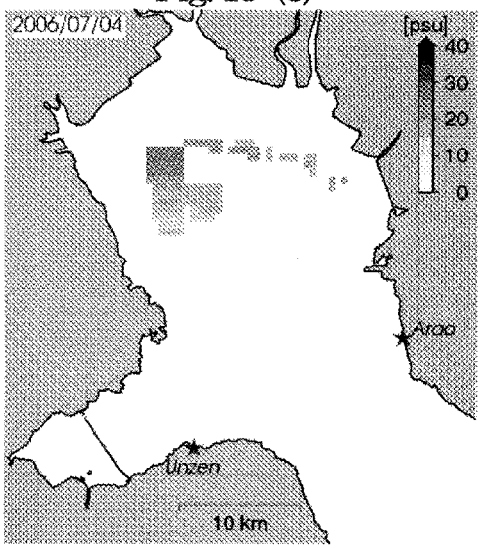

Furthermore, the noise floor of the received power was used to estimate surface layer salinity and obtain a daily mean, whereby results shown FIG. 15 and FIG. 16 were obtained.

Since primary scattering intensity is equal to or below the noise floor at the time of missing observation, the salinity in the marine area is considered to be lower than salinity estimated using the noise floor as received power. Therefore, a salinity value when using the noise floor as the received power will be referred to as a maximum surface layer salinity value.

Assuming that the estimation results on the same day in FIG. 13 and FIG. 14 and those in FIG. 15 and FIG. 16 are continuous north and south, a result that the estimation result of the north side shown in FIG. 15 and FIG. 16 is not extremely discontinuous from the estimation result of the south side shown in FIG. 13 and FIG. 14 was obtained, and it was confirmed that an appropriate value was obtained as the maximum surface layer salinity value.

It was confirmed from the above-described result that the salinity measuring method for marine surface layers according to the present invention enables accurately estimating the salinity in the marine area.

EXAMPLE 2

To verify validity of a water temperature arithmetic result obtained by the water temperature measuring method for marine surface layers according to the present invention, a water temperature arithmetic result using the present invention was compared with an actual measurement result. It is to be noted that electrical conductivity $EC_k=4.0$ $Sm^{-1}$ and temperature correction coefficient $\alpha=0.02$ in this example.

Figure 17:
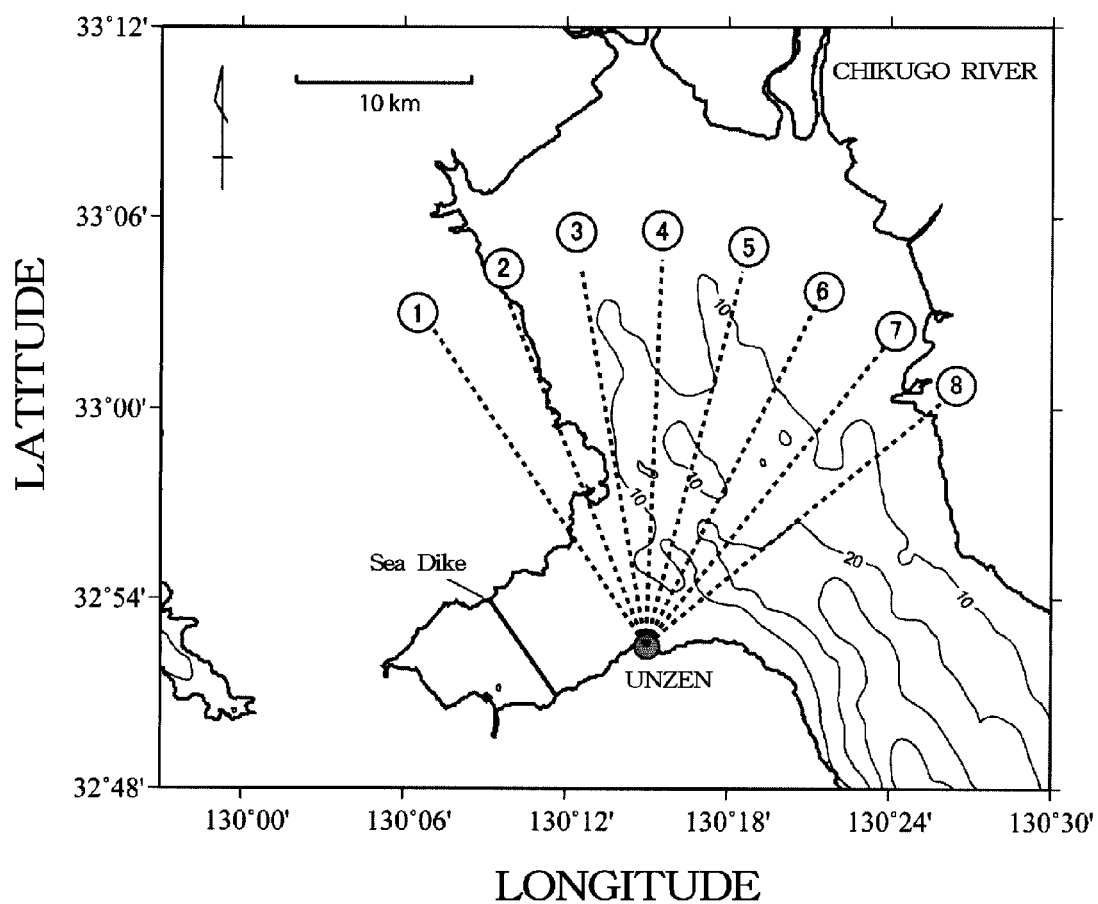
FIG. 17 is a view for explaining an installation position and observing directions of a marine radar according to Example 2.

As observation data of the marine radar, this example used a result of observation carried out at the mouth section of Isahaya bay from December in 2006 to March in 2008 (this period is determined as a measurement time in this example) by using a marine radar installed in Unzen city in Nagasaki Prefecture (a position indicated by a circle symbol immediately above indication of UNZEN in FIG. 17).

A measurement range of the marine radar in Example 2 was as shown in FIG. 17. Further, in Example 2, a water temperature was estimated with respect to <Beam 6, a point of 10 km> of Unzen station. It is to be noted that the marine radar used for the observation, a transmitting/receiving method, detection of primary scattering, and others are equal to those in Example 1.

As reference power, an average value of received power (Takumi Yoshii, et al.: Effect of Surface Layer Salinity in Marine Radar Observation, Research Report of Central Research Institute of Electric Power Industry, V09003, 2009) in observation from June 23 to July 2 in 2007 (this period is determined as a reference time in this example) was used. Referring to actual measurement results of surface layer salinity and a water temperature during this period, a surface layer water temperature is approximately 24° C., electrical conductivity is approximately 4.7 $Sm^{-1}$, and salinity is approximately 31, and it was confirmed that the salinity and the water temperature hardly fluctuated during the reference time.

In Ariake Sea, large-scale overflow from the river is concentrated in the summer season, and surface layer salinity in the marine area in any other season than the summer season is approximately 30 to 32, and there is almost no difference. Therefore, it was assumed that the salinity is 31 and fixed during each of the reference time and the measurement time, and Expression 14 was used for estimation of the water temperature.

On the other hand, as the actual measurement result, water temperature data in Ariake Sea observed from 1995 to 2000 was used (Osamu Kawaguchi, et al.: Characteristics of Water Environment in Poor layer Harvest Year in Kumamoto Coast of Ariake Sea, Oceanography in Japan, 11(2), pp. 543-548, 2002).

Figure 18:
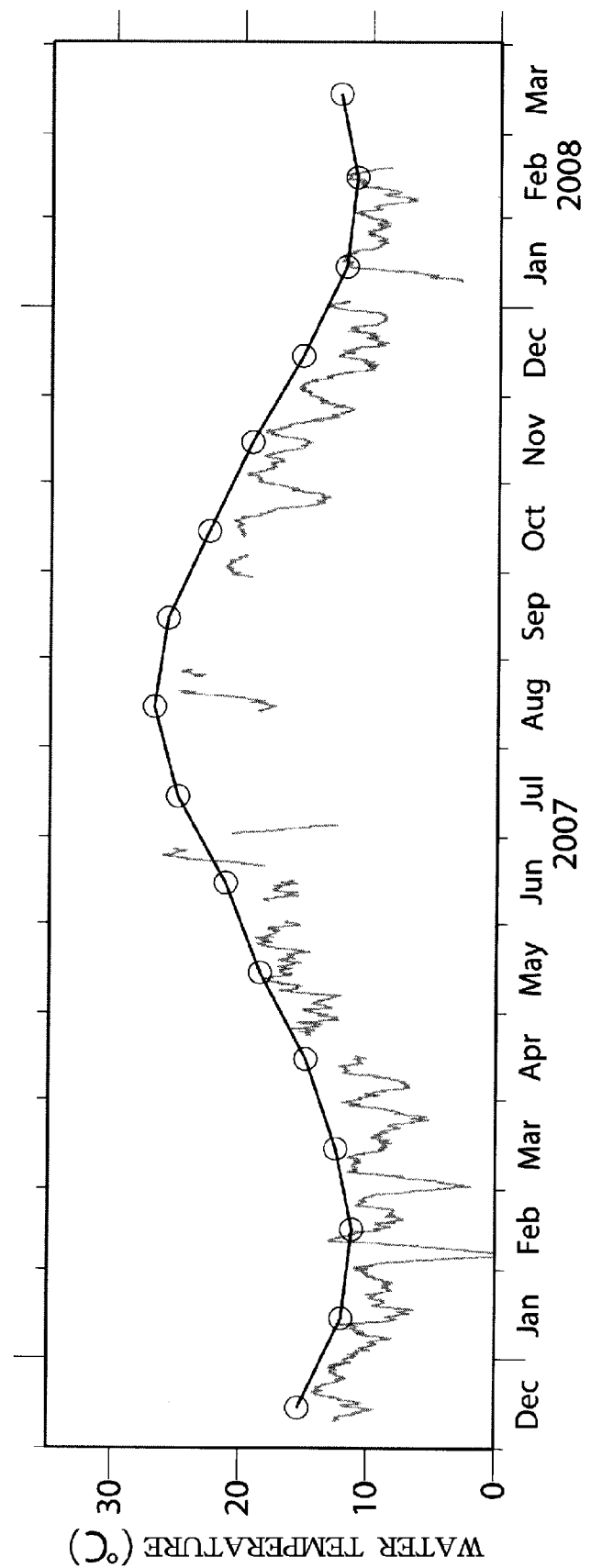
FIG. 18 is a view showing comparison between an estimation result and an actual measurement value of a surface layer water temperature according to Example 2.

When the water temperature value estimated from the received power and the actually measured water temperature data were compared with each other and organized, a result shown in FIG. 18 was obtained (an estimated value: a gray line/an actual measurement value: a white circle symbol, a black line).

It was confirmed from the result of comparison and organization in FIG. 18 that the surface layer water temperature estimated by using the received power of the marine radar at least qualitatively grips seasonal fluctuations in seawater temperature. Based on the above result, it was confirmed that the water temperature measuring method for marine surface layers according to the present invention can correctly estimate a water temperature in the marine area.

REFERENCE SIGNS LIST 10 water quality measuring device
11 control unit
12 storage unit
13 input unit
14 display unit
15 memory
16 data server
17 salinity measuring program for marine surface layer
18 water temperature measuring program for marine surface layer

The invention claimed is:

1. A salinity measuring method for marine surface layers, comprising: a step of estimating a deviation ΔS' by an ocean wave spectrum estimation unit between effect of an ocean wave on primary scattering intensity $RSI_0$' of received power observed by a marine radar in a reference time zone and effect of the ocean wave on primary scattering intensity $RSI_m$' of received power in a measurement time zone by using data of the ocean wave or a wind velocity in the reference time zone in which electrical conductivity of seawater does not change and data of the ocean wave or the wind velocity in the measurement time zone in which water quality of the seawater is measured; a step of estimating a deviation Δs' by an electrical conductivity effect estimation unit between the effect of the ocean wave on the primary scattering intensity $RSI_0$' of the received power in the reference time zone and effect of the ocean wave on primary scattering intensity of the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function f(σ) by the electrical conductivity effect estimation unit of a relationship between primary scattering intensity of the received power obtained by subtracting the deviation Δs' from the primary scattering intensity of the received power observed by the marine radar in the electrical conductivity variable time zone and electrical conductivity σ in the electrical conductivity variable time zone; a step of estimating a value of electrical conductivity $σ_c$ by an electrical conductivity estimation unit in the measurement time zone by using $RSI_0'-RSI_m'=\Delta S'+\{f(\sigma_0)-f(\sigma_c)\}$ (where $\sigma_0$: electrical conductivity in the reference time zone); a step of calculating electrical conductivity $\sigma(15)$ by a temperature correction unit when a water temperature is 15° C. by using the value of the electrical conductivity $\sigma_c$ in the measurement time zone; a step of calculating a ratio $K_{15}$ by an electrical conductivity ratio calculation unit of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and a step of calculating practical salinity by a salinity estimation unit by using the value of the ratio $K_{15}$ of the electrical conductivity.

2. A salinity measuring device for marine surface layers, comprising: means for estimating a deviation $\Delta S'$ between effect of an ocean wave on primary scattering intensity $RSI_0'$ of received power observed by a marine radar in a reference time zone and effect of the ocean wave on primary scattering intensity $RSI_m'$ of received power in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta'$ between the effect of the ocean wave on the primary scattering intensity $RSI_0'$ of the received power in the reference time zone and effect of the ocean wave on primary scattering intensity of the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function $f(\sigma)$ of a relationship between primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and means for calculating practical salinity by using the value of the ratio $K_{15}$ of the electrical conductivity.

3. A salinity measuring program that is stored in a computer-readable storing unit for marine surface layers, which allows a computer, in estimation of salinity in a marine area as a water quality measurement target using a value of received power observed by a marine radar in the marine area, to function as: means for estimating a deviation $\Delta S'$ between effect of an ocean wave on primary scattering intensity $RSI_0'$ of received power observed by the marine radar in a reference time zone and effect of the ocean wave on primary scattering intensity $RSI_m'$ of received power in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the primary scattering intensity $RSI_0'$ of the received power in the reference time zone and effect of the ocean wave on primary scattering intensity of the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function $f(\sigma)$ of a relationship between primary scattering intensity of the received power obtained by subtracting the deviation $\sigma s'$ from the primary scattering intensity of the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and means for calculating practical salinity by using the value of the ratio $K_{15}$ of the electrical conductivity.

4. A water temperature measuring method for marine surface layers comprising: a step of estimating a deviation $\Delta S'$ by an ocean wave spectrum estimation unit between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; a step of estimating a deviation $\Delta s'$ by an electrical conductivity effect estimation unit between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function $f(\sigma)$ by the electrical conductivity effect estimation unit of a relationship between the received power obtained by subtracting the deviation $\Delta s'$ from the received power observed by the marine radar in the electrical conductivity variable time zone and electrical conductivity $\sigma$ in the electrical conductivity variable time zone; a step of estimating a value of electrical conductivity $\sigma_c$ by an electrical conductivity estimation unit in the measurement time zone by using $RSI_0'-RSI_m'=\Delta S'+\{f(\sigma_0)-f(\sigma_c)\}$ (where $\sigma_0$: electrical conductivity in the reference time zone); and a step of estimating a value of a water temperature $T_c$ by a water tempeature estimation unit in the measurement time zone by using $\sigma_c=\sigma_0\{1+\alpha(T_c-T_0)\}$ (where $T_0$: a water temperature in the reference time zone, $\alpha$: a temperature correction coefficient).

5. A water temperature measuring device for marine surface layers, comprising: means for estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; means for estimating a value of electrical conductivity $\sigma_0$ in the measurement time zone by using $RSI_0' - RSI_m' = \Delta S' + \{f(\sigma_0) - f(\sigma^c)\}$ (where $\sigma_0$: electrical conductivity in the reference time zone); and means for estimating a value of a water temperature $T_c$ in the measurement time zone by using $\sigma_c = \sigma_0\{1 + \alpha(T_c - T_0)\}$ (where $T_0$: a water temperature in the reference time zone, $\alpha$: a temperature correction coefficient).

6. A water temperature measuring that is stored in a computer-readable storing unit program for marine surface layers, which allows a computer, in estimation of a water temperature in a marine area as a water quality measurement target using a value of received power observed by a marine radar in the marine area, to function as: means for estimating a deviation $\Delta S'$ between effect of an ocean wave on received power $RSI_0'$ observed by the marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function $f(\sigma)$ of a relationship between the received power obtained by subtracting the deviation $\Delta s'$ from the received power observed by the marine radar in the electrical conductivity variable time zone and electrical conductivity a in the electrical conductivity variable time zone; means for estimating a value of electrical conductivity $\sigma_c$ in the measurement time zone by using $RSI_0' - RSI_m' = \Delta S' + \{f(\sigma_0) - f(\sigma^0)\}$ (where $\sigma_0$: electrical conductivity in the reference time zone); and means for estimating a value of a water temperature $T_c$ in the measurement time zone by using $\sigma_c = \sigma_0\{1 + \alpha(T_c - T_0)\}$ (where $T_0$: a water temperature in the reference time zone, $\alpha$: a temperature correction coefficient).

7. A water temperature measuring method for marine surface layers, comprising: a step of estimating a deviation $\Delta S'$ by an ocean wave spectrum estimation unit between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; a step of estimating a deviation $\Delta s'$ by an electrical conductivity effect estimation unit between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; a step of estimating a regression function $f(\sigma)$ by the electrical conductivity effect estimation unit of a relationship between the received power obtained by subtracting the deviation $\Delta s'$ from the received power observed by the marine radar in the electrical conductivity variable time zone and electrical conductivity $\sigma$ in the electrical conductivity variable time zone; a step of estimating a value of electrical conductivity $\sigma_c$ by an electrical conductivity estimation unit in the measurement time zone by using $RSI_0' - RSI_m' = \Delta S' + \{f(\sigma^0) - f(\sigma^c)\}$ (where $\sigma_0$: electrical conductivity in the reference time zone); and a step of estimating a value of a water temperature $T_c$ by a water temperature estimation unit in the measurement time zone by using $K_{15} = \sigma^c/[\sigma_{KCl}(15)\{1 + \alpha(T_c - 15)\}]$ and $PS = 0.008 - 0.1692 K_{15}^{0.5} + 25.3851 K_{15} + 14.0941 K_{15}^{1.5} - 7.0261 K_{15}^2 + 2.7081 K_{15}^{2.5}$ (where $\sigma_{KCl}(15)$: electrical conductivity of a standard solution of a potassium chloride in a standard state of 15° C. and 1 atmosphere, $\alpha$: a temperature correction coefficient, PS: salinity in the measurement time zone).

8. A water temperature measuring device for marine surface layers, comprising: means for estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0' - RSI_m' = \Delta S' + \{f(\sigma_0) - f(\sigma_c)\}$ (where $\sigma_0$: electrical conductivity in the reference time zone); and means for estimating a value of a water temperature $T_c$ in the measurement time zone by using $K_{15} = \sigma_c/[S_{KCl}(15)\{1 + \alpha(T_c - 15)\}]$ and $PS = 0.008 - 0.1692 K_{15}^{0.5} + 25.3851 K_{15} + 14.0941 K_{15}^{1.5} - 7.0261 K_{15}^2 + 2.7081 K_{15}^{2.5}$ (where $\sigma_{KCl}(15)$: electrical conductivity of a standard solution of a potassium chloride in a standard state of 15° C. and 1 atmosphere, $\alpha$: a temperature correction coefficient, PS: salinity in the measurement time zone).

9. A water temperature measuring program that is stored in a computer-readable storing unit for marine surface layers, which allows a computer, in estimation of a water temperature in a marine area as a water quality measurement target using a value of received power observed by the marine radar in the marine area, to function as: means for estimating a deviation $\Delta S'$ between effect of an ocean wave on received power $RSI_0'$ observed by a marine radar in a reference time zone and effect of the ocean wave on received power $RSI_m'$ in a measurement time zone by using data of the ocean wave or a wind velocity in the reference time zone in which electrical conductivity of seawater does not change and data of the ocean wave or the wind velocity in the measurement time zone in which water quality of the seawater is measured; means for estimating a deviation $\Delta s'$ between the effect of the ocean wave on the received power $RSI_0'$ in the reference time zone and effect of the ocean wave on the received power in an electrical conductivity variable time zone by using data of the ocean wave or the wind velocity in the reference time zone and data of the ocean wave or the wind velocity in the electrical conductivity variable time zone in which the electrical conductivity of the seawater varies; means for estimating a regression function $f(\sigma)$ of a relationship between the received power obtained by subtracting the deviation $\Delta s'$ from the received power observed by the marine radar in the electrical conductivity variable time zone and electrical conductivity $\sigma$ in the electrical conductivity variable time zone; means for estimating a value of electrical conductivity $\sigma_c$ in the measurement time zone by using $RSI_0'-RSI_m'=\Delta S'+\{f(\sigma_0)-f(\sigma_c)\}$ (where $\sigma_0$: electrical conductivity in the reference time zone); and means for estimating a value of a water temperature $T_c$ in the measurement time zone by using $K_{15}=\sigma_c/[\sigma_{KCl}(15)\{1+\alpha(T_c-15)\}]$ and $PS=0.008-0.1692K_{15}^{0.5}+25.3851K_{15}+14.0941K_{15}^{1.5}-7.0261K_{15}^{2}+2.7081K_{15}^{2.5}$ (where $s_{KCl}(15)$: electrical conductivity of a standard solution of a potassium chloride in a standard state of 15° C. and 1 atmosphere, $\alpha$: a temperature correction coefficient, PS: salinity in the measurement time zone).

10. A salinity measuring method for marine surface layers, comprising: a step of estimating a deviation $\Delta s'$ by an electrical conductivity effect estimation unit between effect of an ocean wave on primary scattering intensity $RSI_0'$ of received power observed by a marine radar in a reference time zone and effect of the ocean wave on the primary scattering intensity of the received power in an electrical conductivity variable time zone by using data of the ocean wave or a wind velocity in the reference time zone that electrical conductivity of seawater does not change and data of the ocean wave or the wind velocity in the electrical conductivity variable time zone in which the electrical conductivity of the seawater varies; a step of estimating a regression function $f(\sigma)$ by the electrical conductivity effect estimation unit of a relationship between the primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; a step of estimating a value of electrical conductivity $\sigma_c$ by an electrical conductivity estimation unit in a measurement time zone by using a noise floor $RSIn_m'$ of the received power in the measurement time zone in which water quality of the seawater is measured and $RSI_0'-RSIn_m'=f(\sigma_0)-f(\sigma_c)$ (where $\sigma_0$: electrical conductivity in the reference time zone); a step of calculating electrical conductivity $\sigma(15)$ by a temperature correction unit when a water temperature is 15° C. by using the value of the electrical conductivity $\sigma_c$ in the measurement time zone; a step of calculating a ratio $K_{15}$ of the electrical conductivity $\sigma(15)$ by an electrical conductivity ratio calculation unit of the seawater to electrical conductivity of a standard solution of a potassium chloride in a standard state of 15° C. and 1 atmosphere by using the electrical conductivity $\sigma(15)$ when the water temperature is 15° C.; and a step of calculating practical salinity by a salinity estimation unit using the value of the ratio $K_{15}$ of the electrical conductivity.

11. A salinity measuring device for marine surface layers, comprising: means for estimating a deviation $\Delta s'$ between effect of an ocean wave on primary scattering intensity $RSI_0'$ of received power observed by a marine radar in a reference time zone and effect of the ocean wave on the primary scattering intensity of the received power in an electrical conductivity variable time zone by using data of the ocean wave or a wind velocity in the reference time zone that electrical conductivity of seawater does not change and data of the ocean wave or the wind velocity in the electrical conductivity variable time zone in which the electrical conductivity of the seawater varies; means for estimating a regression function $f(\sigma)$ of a relationship between the primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; means for estimating a value of electrical conductivity $\sigma_c$ in a measurement time zone by using a noise floor $RSIn_m'$ of the received power in the measurement time zone in which water quality of the seawater is measured and $RSI_0'-RSIn_m'=f(\sigma_0)-f(\sigma_c)$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and means for calculating practical salinity by using the value of the ratio $K_{15}$ of the electrical conductivity.

12. A salinity measuring program that is stored in a computer-readable storing unit for marine surface layers, which allows a computer, in estimation of salinity in a marine area as a water quality measurement target using a value of received power observed by a marine radar in the marine area, to function as: means for estimating a deviation $\Delta s'$ between effect of an ocean wave on primary scattering intensity $RSI_0'$ of received power observed by the marine radar in a reference time zone and effect of the ocean wave on the primary scattering intensity of the received power in an electrical conductivity variable time zone by using data of the ocean wave or a wind velocity in the reference time zone that electrical conductivity of seawater does not change and data of the ocean wave or the wind velocity in the electrical conductivity variable time zone in which the electrical conductivity of the seawater varies; means for estimating a regression function $f(\sigma)$ of a relationship between the primary scattering intensity of the received power obtained by subtracting the deviation $\Delta s'$ from the primary scattering intensity of the received power observed by the marine radar in the electrical conductivity variable time zone and electrical conductivity $\sigma$ in the electrical conductivity variable time zone; means for estimating a value of electrical conductivity $\sigma_c$ in a measurement time zone by using a noise floor $RSIn_m'$ of the received power in the measurement time zone in which water quality of the seawater is measured and $RSI_0'-RSIn_{m'=f(\infty)}-f(\sigma_c)$ (where $\sigma_0$: electrical conductivity in the reference time zone); means for calculating electrical conductivity $\sigma(15)$ when a water temperature is 15° C. by using the value of the electrical conductivity $\sigma_c$ in the measurement time zone; means for calculating a ratio $K_{15}$ of the electrical conductivity $\sigma(15)$ of the seawater to electrical conductivity of a standard solution of a potassium chloride in a standard state of 15° C. and 1 atmosphere by using the electrical conductivity $\sigma(15)$ when the water temperature is 15° C.; and means for calculating practical salinity by using the value of the ratio $K_{15}$ of the electrical conductivity.

\* \* \* \* \*